(12) United States Patent
Iwasaki et al.

(10) Patent No.: US 7,961,412 B2
(45) Date of Patent: Jun. 14, 2011

(54) ACTUATOR APPARATUS AND IMAGE PICKUP UNIT

(75) Inventors: Seiji Iwasaki, Hachioji (JP); Toru Kuchimaru, Hachioji (JP); Yuuya Ishida, Hachioji (JP); Seiji Sakai, Chofu (JP)

(73) Assignee: Olympus Medical Systems Corp., Tokyo (JP)

( * ) Notice: Subject to any disclaimer, the term of this patent is extended or adjusted under 35 U.S.C. 154(b) by 65 days.

(21) Appl. No.: 12/478,406

(22) Filed: Jun. 4, 2009

(65) Prior Publication Data

US 2009/0303619 A1    Dec. 10, 2009

(30) Foreign Application Priority Data

Jun. 4, 2008   (JP) .................................. 2008-147216

(51) Int. Cl.
*G02B 7/02* (2006.01)
*A61B 1/00* (2006.01)

(52) U.S. Cl. ........ 359/820; 359/824; 359/554; 359/557; 359/696; 600/151; 348/65; 396/132; 396/418; 60/527

(58) Field of Classification Search .................. 359/820, 359/823, 824, 831, 554, 557; 396/52, 55, 396/72, 132, 177, 418; 60/527–529; 62/222, 62/513, 527; 348/65, 340, E5.046; 310/306; 604/890.1
See application file for complete search history.

(56) References Cited

U.S. PATENT DOCUMENTS

| 4,914,908 | A | * | 4/1990 | Sugiyama et al. ............. 60/527 |
| 4,965,545 | A | * | 10/1990 | Johnson ........................ 337/140 |
| 5,312,152 | A | * | 5/1994 | Woebkenberg et al. ..... 294/86.4 |
| 5,531,664 | A | * | 7/1996 | Adachi et al. ................. 600/149 |
| 5,577,992 | A | * | 11/1996 | Chiba et al. ................... 600/152 |
| 6,307,678 | B2 | * | 10/2001 | Kosaka et al. ................ 359/557 |
| 6,434,333 | B2 | * | 8/2002 | Tanaka et al. ................. 396/132 |
| 6,516,146 | B1 | * | 2/2003 | Kosaka .......................... 396/55 |
| 6,945,045 | B2 | * | 9/2005 | Hara et al. ..................... 60/527 |
| 7,663,811 | B2 | * | 2/2010 | Noda et al. .................... 359/696 |
| 2007/0100209 | A1 | | 5/2007 | Takahashi et al. |
| 2007/0149855 | A1 | | 6/2007 | Noguchi et al. |
| 2009/0076332 | A1 | * | 3/2009 | Iwasaki et al. ................ 600/168 |
| 2009/0185032 | A1 | * | 7/2009 | Sakai et al. .................... 348/65 |

FOREIGN PATENT DOCUMENTS

| JP | 63-206728 | 8/1988 |
| JP | 11-197096 | 7/1999 |
| JP | 2007-229155 | 9/2007 |
| JP | 2007-292864 | 11/2007 |

* cited by examiner

*Primary Examiner* — Loha Ben
(74) *Attorney, Agent, or Firm* — Scully, Scott, Murphy & Presser, P.C.

(57) ABSTRACT

An actuator apparatus of the present invention includes a movable body that is arranged so as to be movable forward or rearward, and a shape memory alloy wire that is provided directly or indirectly to the movable body so as to enter a non-tension state at an ordinary temperature. The shape memory alloy wire is subjected to expansion/contraction control in which an electric current is applied thereto from a power supply portion of an external control circuit portion to change a temperature thereof to a predetermined temperature.

9 Claims, 24 Drawing Sheets

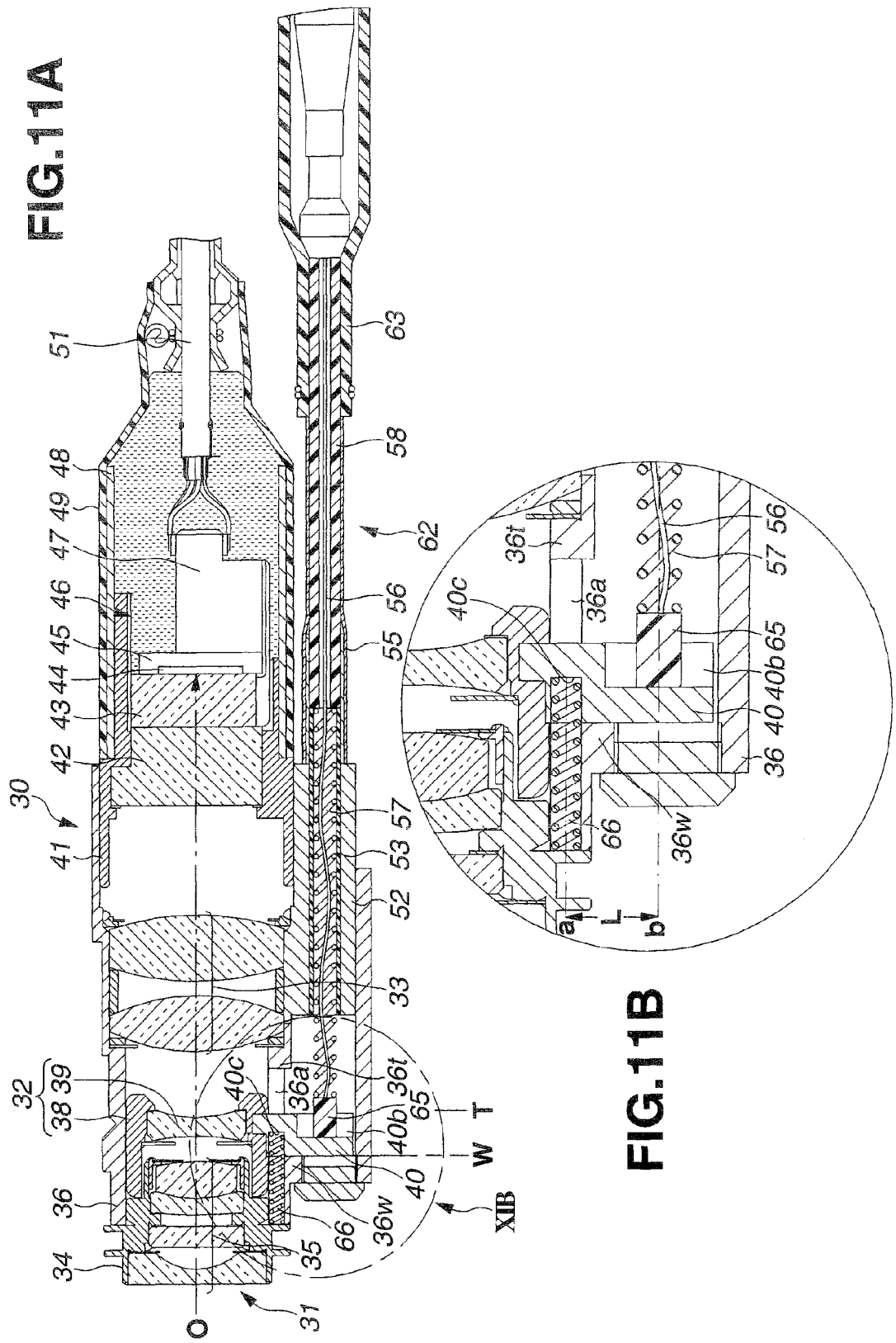

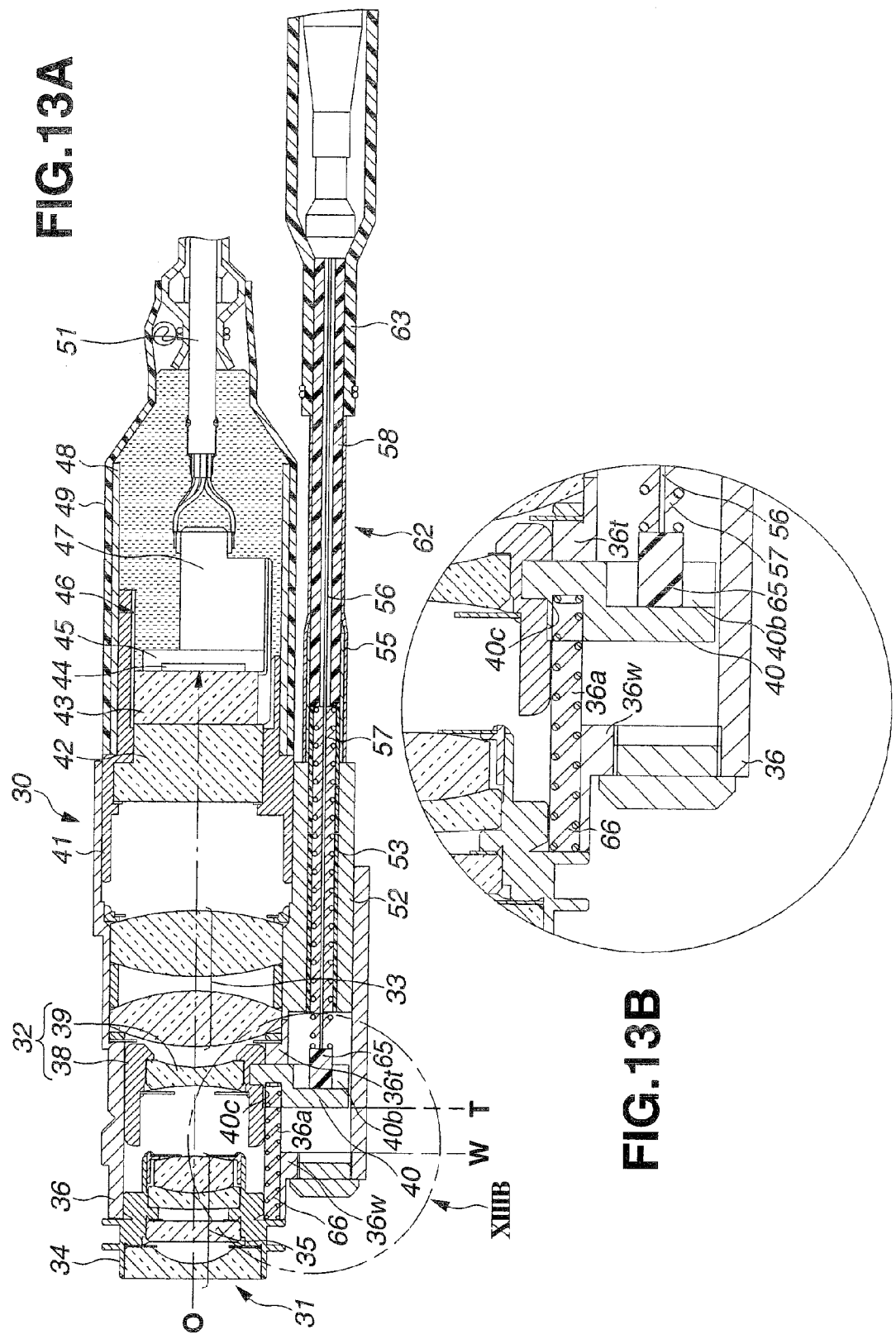

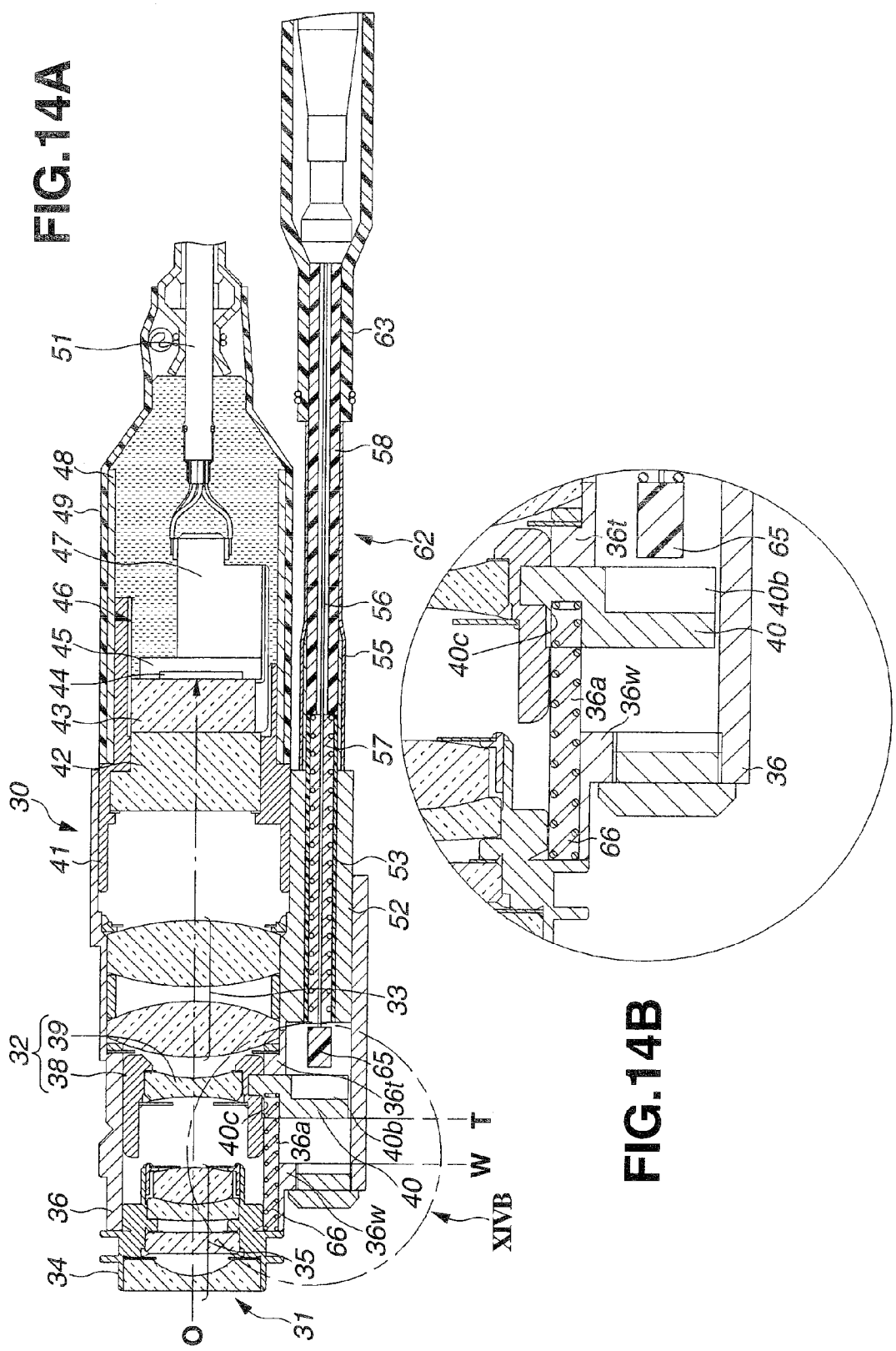

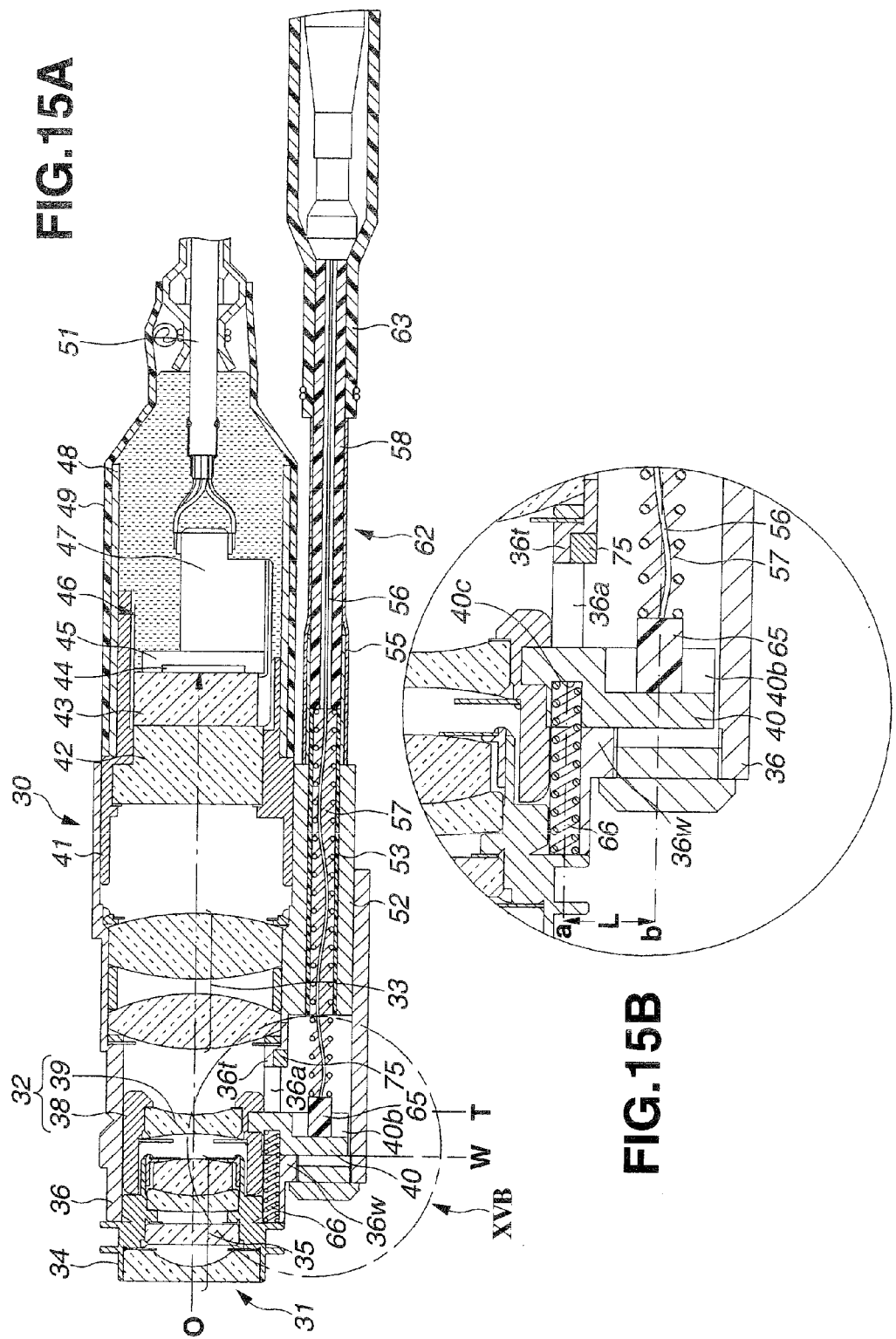

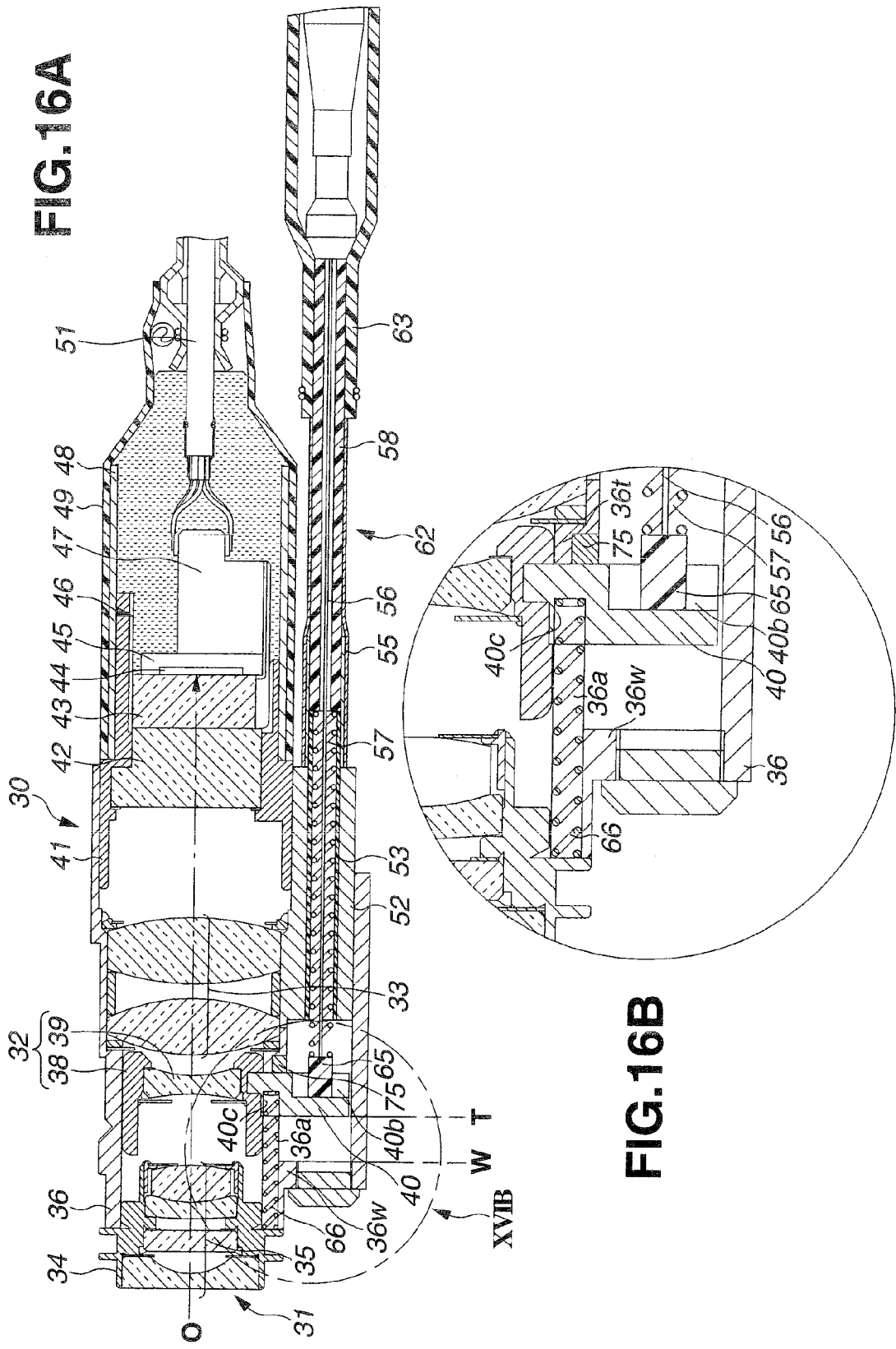

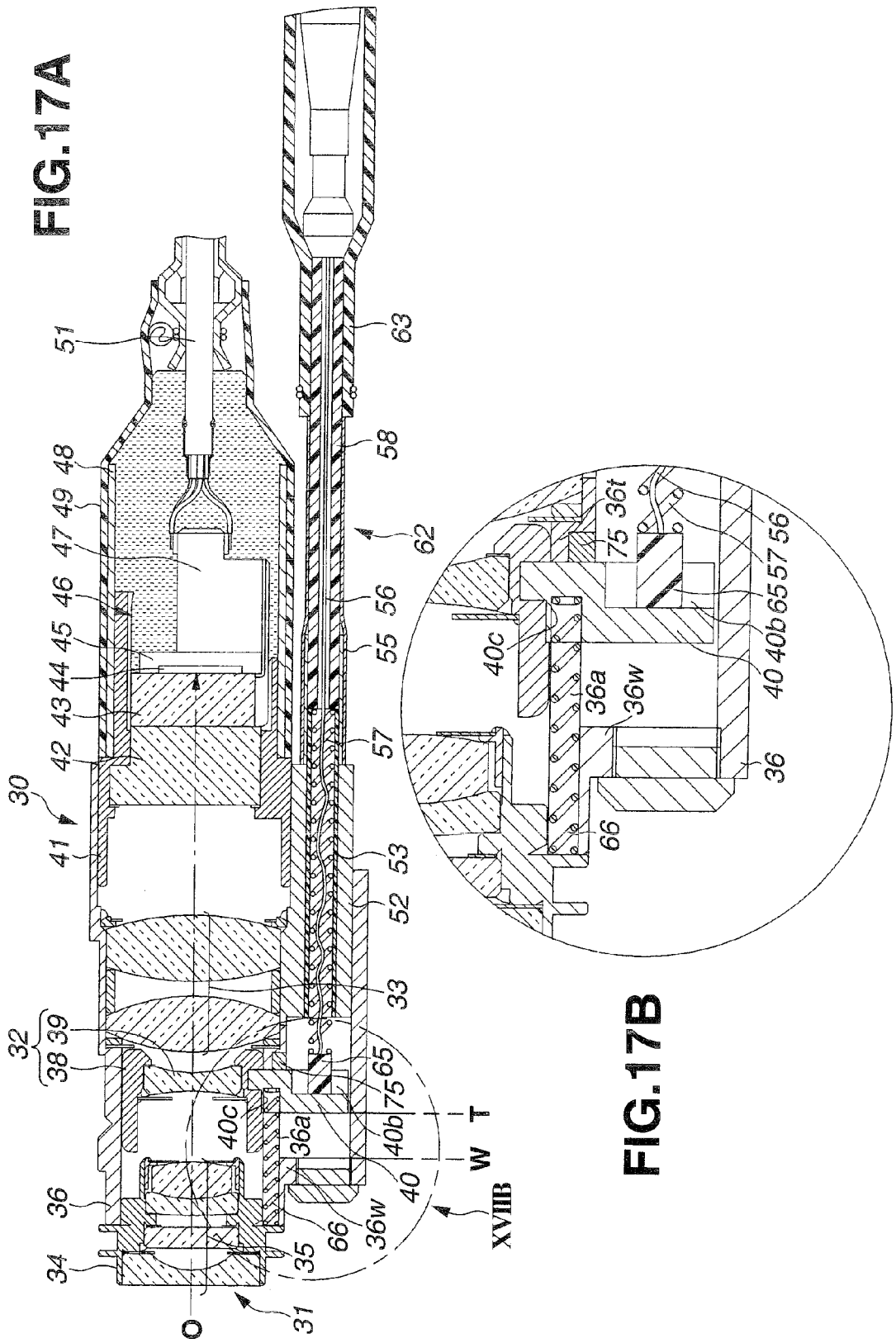

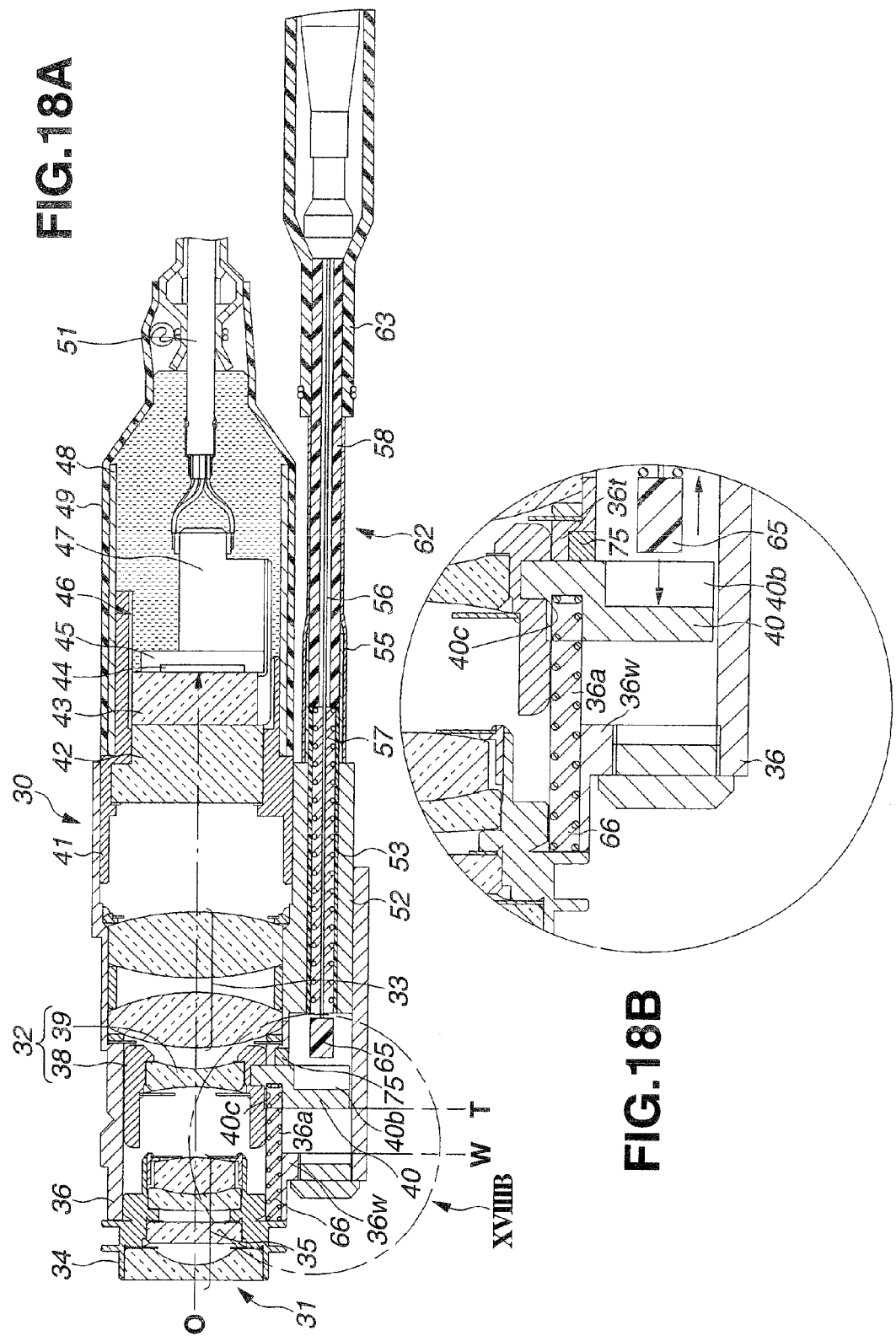

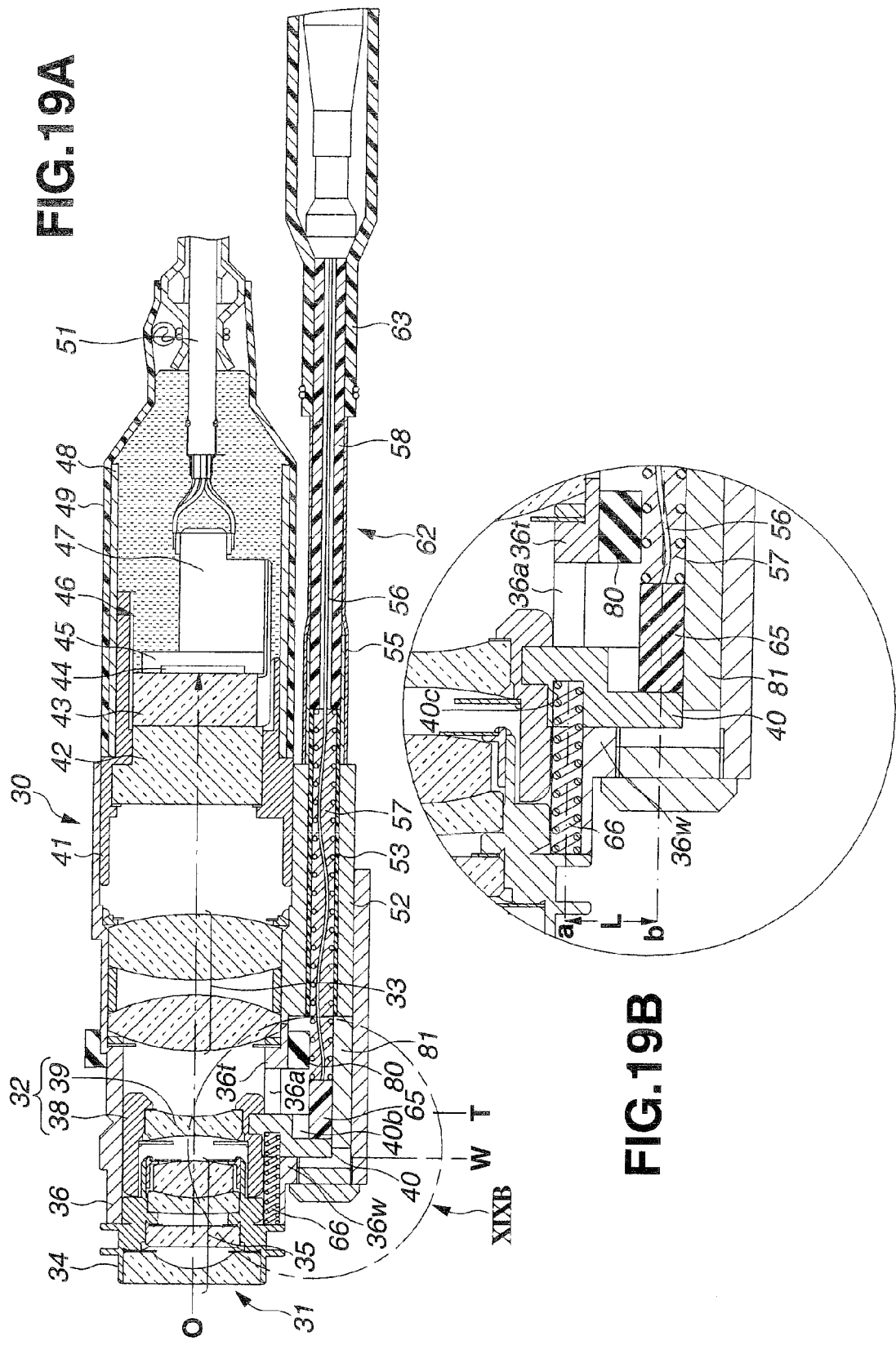

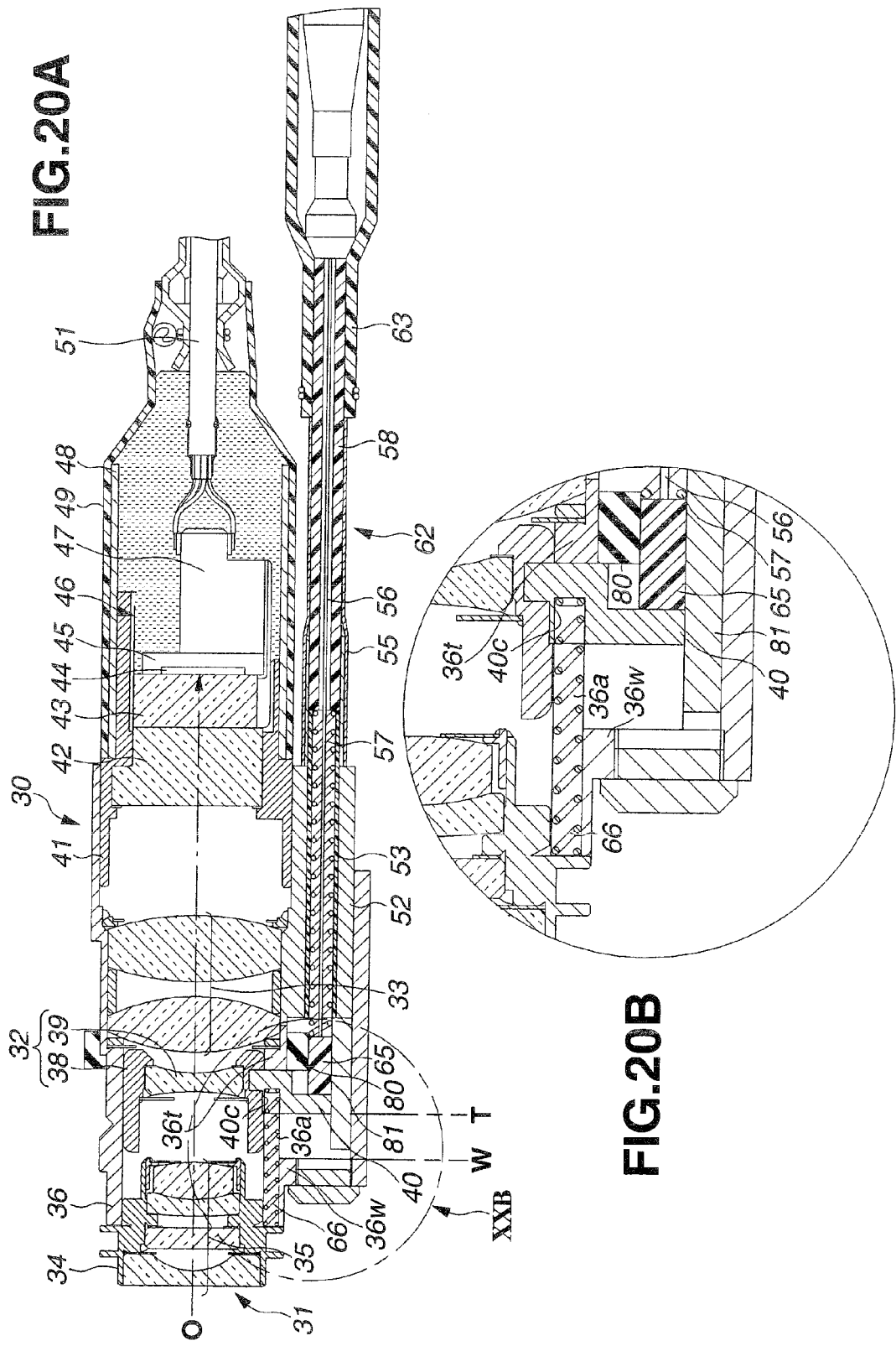

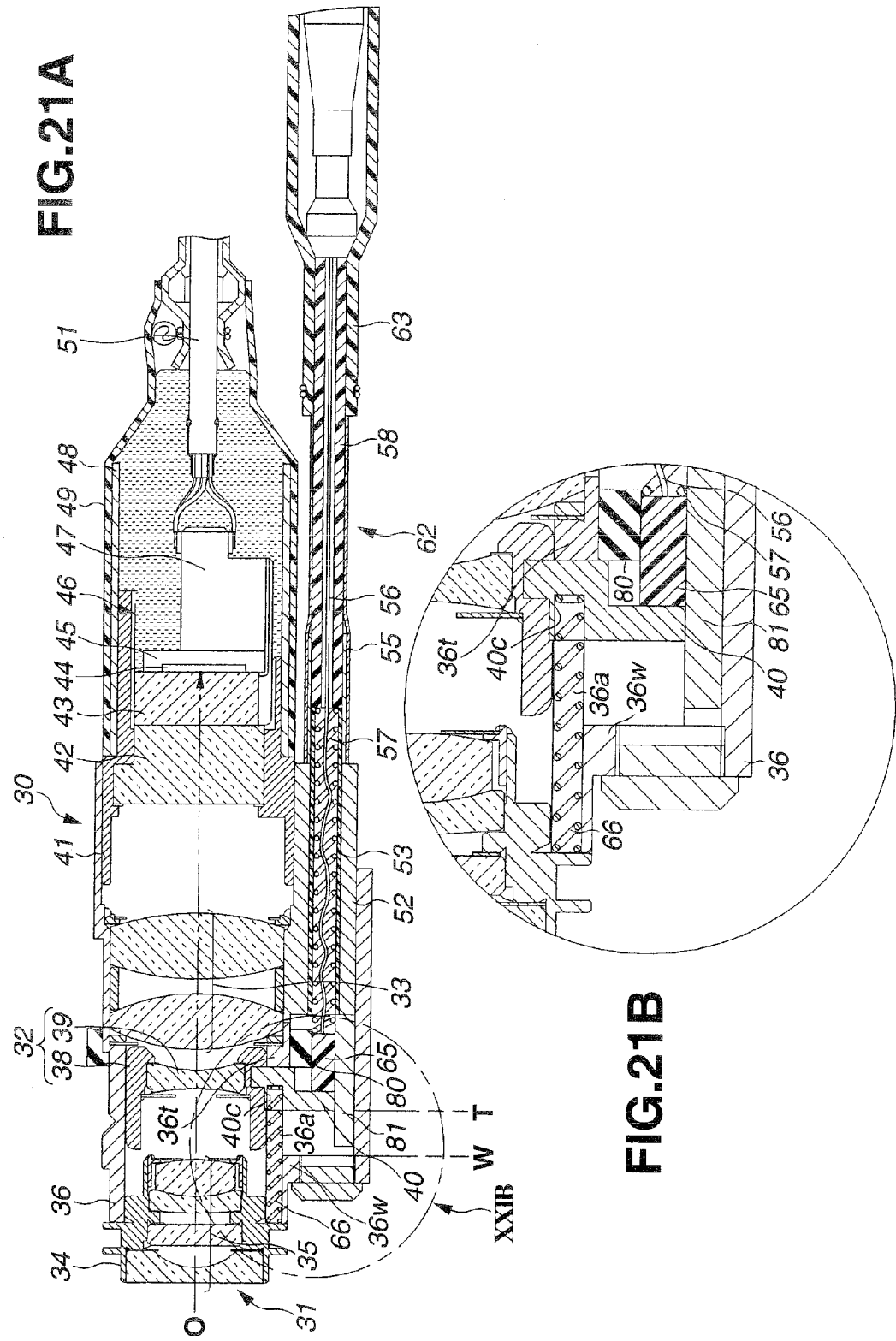

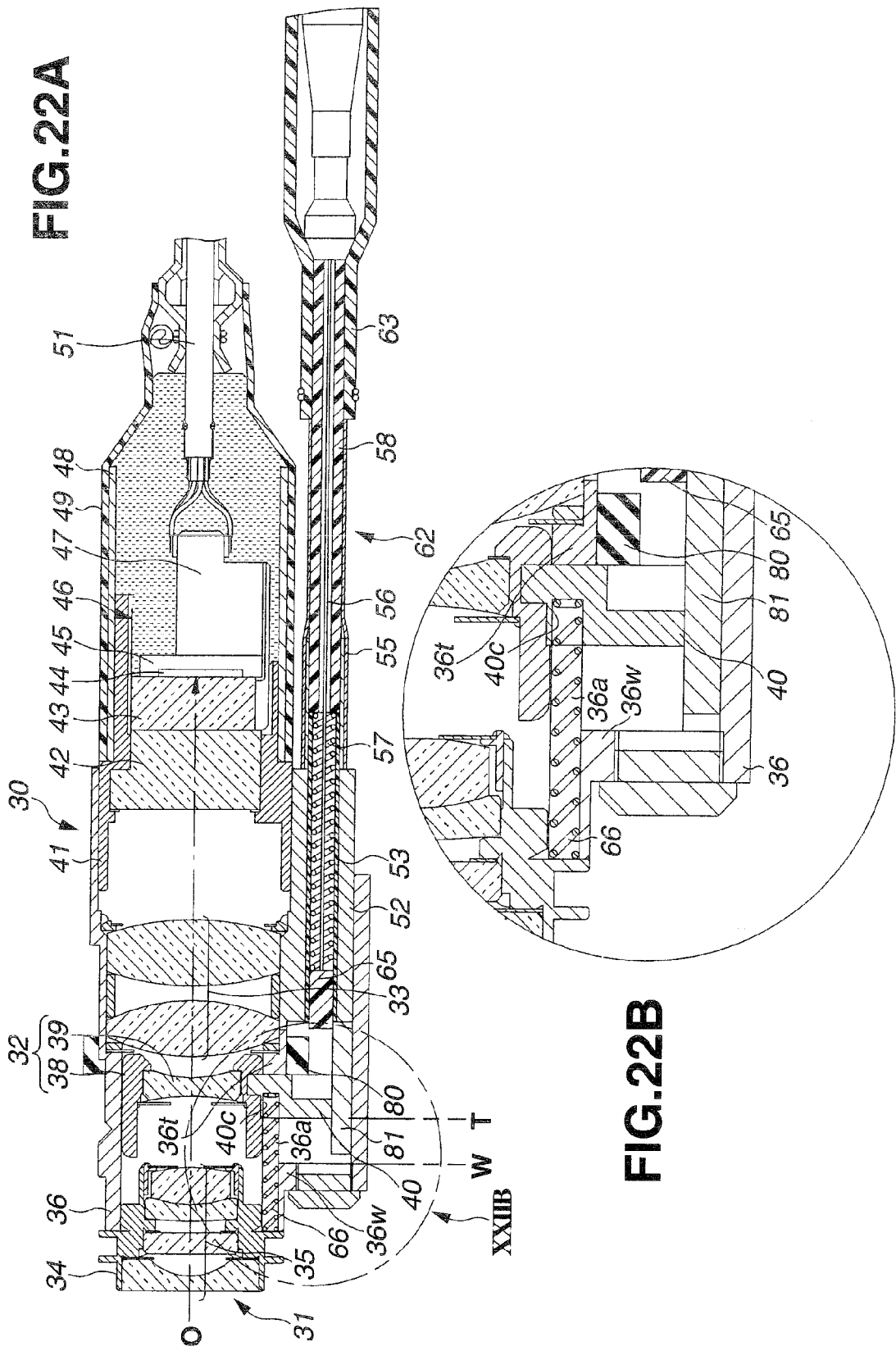

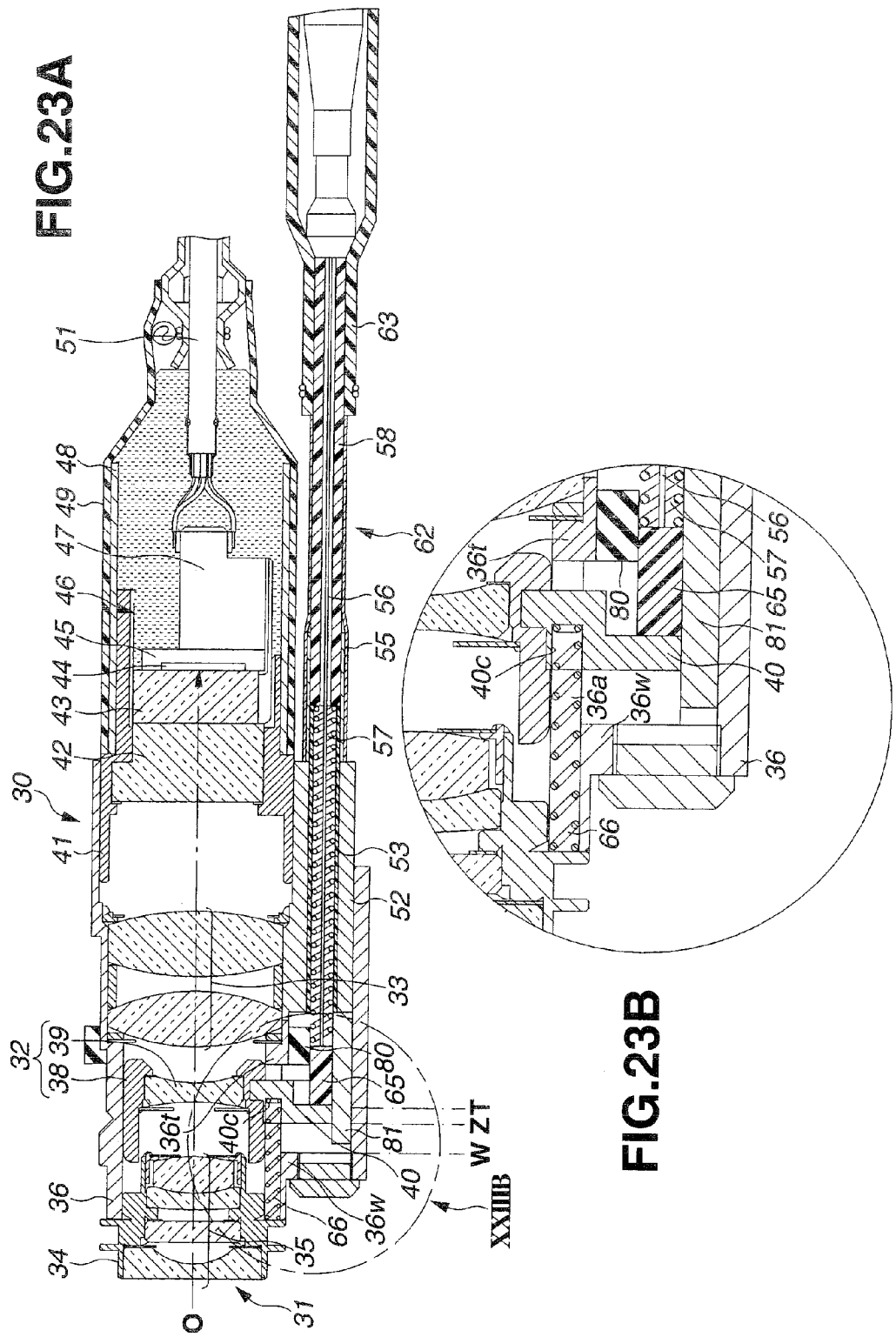

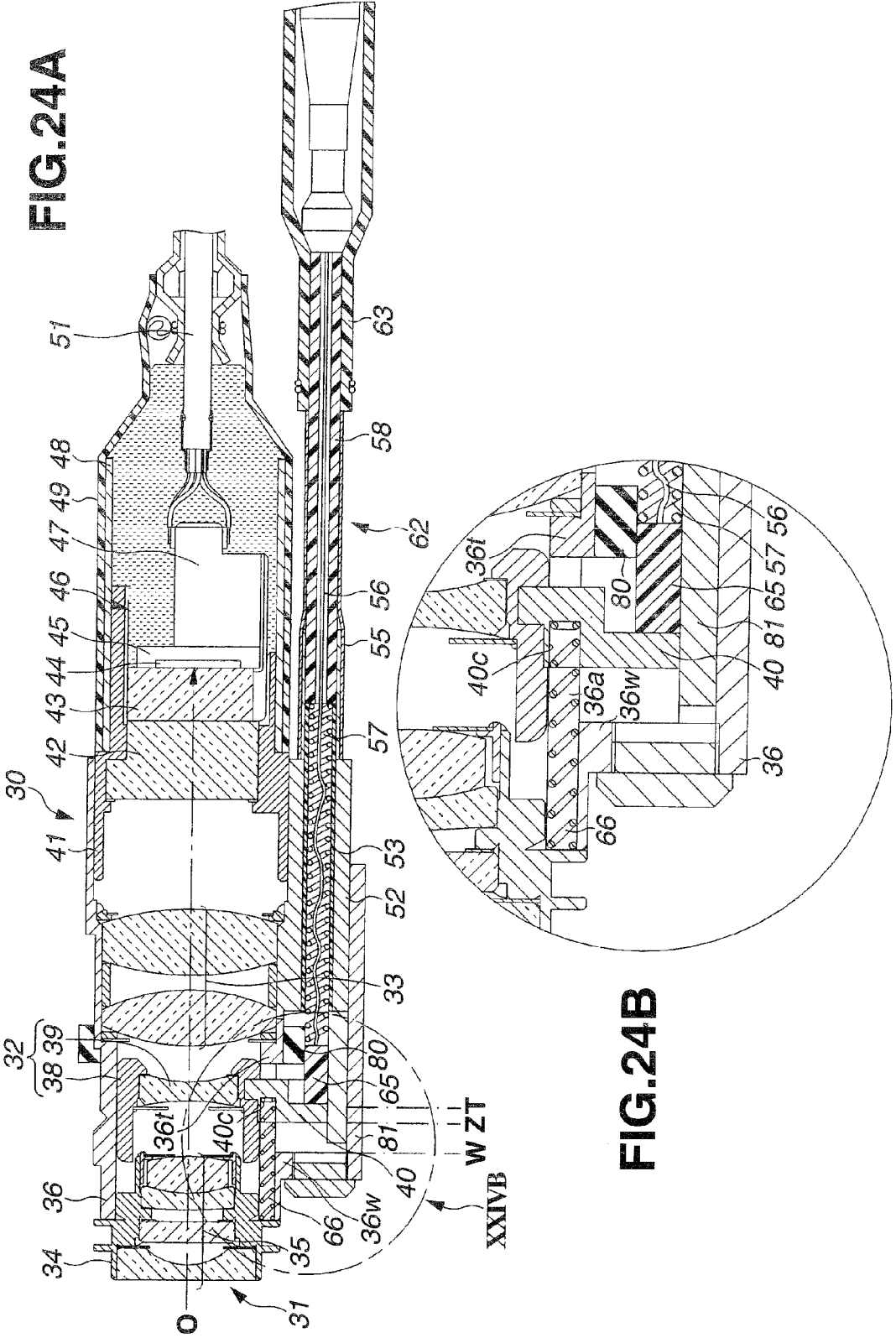

ACTUATOR APPARATUS AND IMAGE PICKUP UNIT

This application claims benefit of Japanese Application No. 2008-147216 filed in Japan on Jun. 4, 2008, the contents of which are incorporated by this reference.

BACKGROUND OF THE INVENTION

1. Field of the Invention

The present invention relates to an actuator apparatus that adjusts optical properties of an objective optical system, and an image pickup unit that are arranged in an endoscope.

2. Description of the Related Art

As is known, electronic endoscopes are widely used for observing and/or treating the inside of (body cavities of) living organisms or for examining and/or repairing the inside of industrial plant facilities and the like. In recent years, in some electronic endoscopes an image pickup unit is used that can change a focal length for a focusing function that adjusts a focus of a photographing object or a zooming function that implements wide zooming/telescopic zooming by moving an observation optical system in the direction of the photographing optical axis.

This kind of technology that moves a movable lens frame to adjust optical properties for a zooming function or the like in an image pickup unit provided in an endoscope is disclosed, for example, in Japanese Patent Application Laid-Open Publication No. 2007-229155.

The aforementioned Japanese Patent Application Laid-Open Publication No. 2007-229155 discloses technology of an endoscope that utilizes an urging spring and a shape memory alloy (hereunder, referred to as "SMA") wire as an actuator apparatus for moving forward and backward a movable lens frame that retains a movable lens for adjusting the optical properties.

According to this conventional image pickup unit of an endoscope, the movable lens frame is moved backward against the urging force of the urging spring when the SMA wire is caused to contract by passing a current thereto. Further, when the current being passed to the contracted SMA wire is stopped to cause the SMA wire to expand, the movable lens frame is moved forward by the urging force of the urging spring. In this manner, an optical property such as a zooming function is adjusted.

SUMMARY OF THE INVENTION

An actuator apparatus according to the present invention includes a movable body that is movable forward or backward, and a shape memory alloy wire that is directly or indirectly provided to the movable body so as to enter a non-tension state at an ordinary temperature and which is subjected to expansion/contraction control in which an electric current is applied thereto from a power supply portion of an external control circuit portion to change a temperature of the shape memory alloy wire to a predetermined temperature.

An image pickup unit according to the present invention includes a movable lens unit that has an optical lens and that moves the optical lens forward and backward in an optical axis direction, a first elastic member that urges the movable lens unit forward, a second elastic member that urges the movable lens unit backward and is provided on an axis that is parallel to and different from an axis of the first elastic member and that has a smaller urging force than the first elastic member, and a shape memory alloy wire that is provided directly or indirectly to the movable lens unit and that pulls the movable lens unit rearward at a time of contraction upon being subjected to expansion/contraction control in which an electric current is applied thereto from a power supply portion of an external control circuit portion to change a temperature thereof to a predetermined temperature.

The above and other objects, features and advantages of the invention will become more clearly understood from the following description referring to the accompanying drawings.

BRIEF DESCRIPTION OF THE DRAWINGS

FIG. 11A is a sectional view showing the configuration of an image pickup unit according to a second embodiment;

FIG. 11B is an enlarged view of a portion surrounded by a circle XIA in FIG. 11A according to the second embodiment;

FIG. 13A is a sectional view of the image pickup unit for describing an action whereby the movable lens frame moves to a telescopic end position according to the second embodiment;

FIG. 13B is an enlarged view of a portion surrounded by a circle XIIIA in FIG. 13A according to the second embodiment;

FIG. 14A is a sectional view of the image pickup unit that illustrates a state in which the movable lens frame has moved to a telescopic end position according to the second embodiment;

FIG. 14B is an enlarged view of a portion surrounded by a circle XIVA in FIG. 14A according to the second embodiment;

FIG. 15A is a sectional view showing the configuration of an image pickup unit according to a third embodiment;

FIG. 15B is an enlarged view of a portion surrounded by a circle XVA in FIG. 15A according to the third embodiment;

FIG. 16A is a sectional view of an image pickup unit for describing an action whereby a movable lens frame moves to a telescopic end position according to the third embodiment;

FIG. 16B is an enlarged view of a portion surrounded by a circle XVIA in FIG. 16A according to the third embodiment;

FIG. 17A is a sectional view of the image pickup unit that illustrates a state in which application of an electric current to an SMA wire is stopped in a state in which the movable lens frame has moved to the telescopic end position according to the third embodiment;

FIG. 17B is an enlarged view of a portion surrounded by a circle XVIIA in FIG. 17A according to the third embodiment;

FIG. 18A is a sectional view of the image pickup unit that illustrates a state in which an electric current is applied to the SMA wire again, in a state in which the movable lens frame has moved to the telescopic end position according to the third embodiment;

FIG. 18B is an enlarged view of a portion surrounded by a circle XVIIIA in FIG. 18A according to the third embodiment;

FIG. 19A is a sectional view showing the configuration of an image pickup unit according to a fourth embodiment;

FIG. 19B is an enlarged view of a portion surrounded by a circle XIXA in FIG. 19A according to the fourth embodiment;

FIG. 20A is a sectional view of an image pickup unit for describing an action whereby a movable lens frame moves to a telescopic end position according to the fourth embodiment;

FIG. 20B is an enlarged view of a portion surrounded by a circle XXA in FIG. 20A according to the fourth embodiment;

FIG. 21A is a sectional view of the image pickup unit that illustrates a state in which application of an electric current to an SMA wire is stopped in a state in which the movable lens frame has moved to the telescopic end position according to the fourth embodiment;

FIG. 21B is an enlarged view of a portion surrounded by a circle XXIA in FIG. 21A according to the fourth embodiment;

FIG. 22A is a sectional view of the image pickup unit that illustrates a state in which an electric current is applied to the SMA wire again, in a state in which the movable lens frame has moved to the telescopic end position according to the fourth embodiment;

FIG. 22B is an enlarged view of a portion surrounded by a circle XXIIA in FIG. 22A according to the fourth embodiment;

FIG. 23A is a sectional view of the image pickup unit for describing an action whereby the movable lens frame moves to an arbitrary optical property position according to the fourth embodiment;

FIG. 23B is an enlarged view of a portion surrounded by a circle XXIIIA in FIG. 23A according to the fourth embodiment;

FIG. 24A is a sectional view of the image pickup unit that illustrates a state in which application of an electric current to the SMA wire is stopped in a state in which the movable lens frame has moved to the arbitrary optical property position according to the fourth embodiment; and FIG. 24B is an enlarged view of a portion surrounded by a circle XXIVA in FIG. 24A according to the fourth embodiment.

DETAILED DESCRIPTION OF THE PREFERRED EMBODIMENTS

Hereunder, the present invention is described using embodiments based on the attached drawings.

First Embodiment

Figure 1:
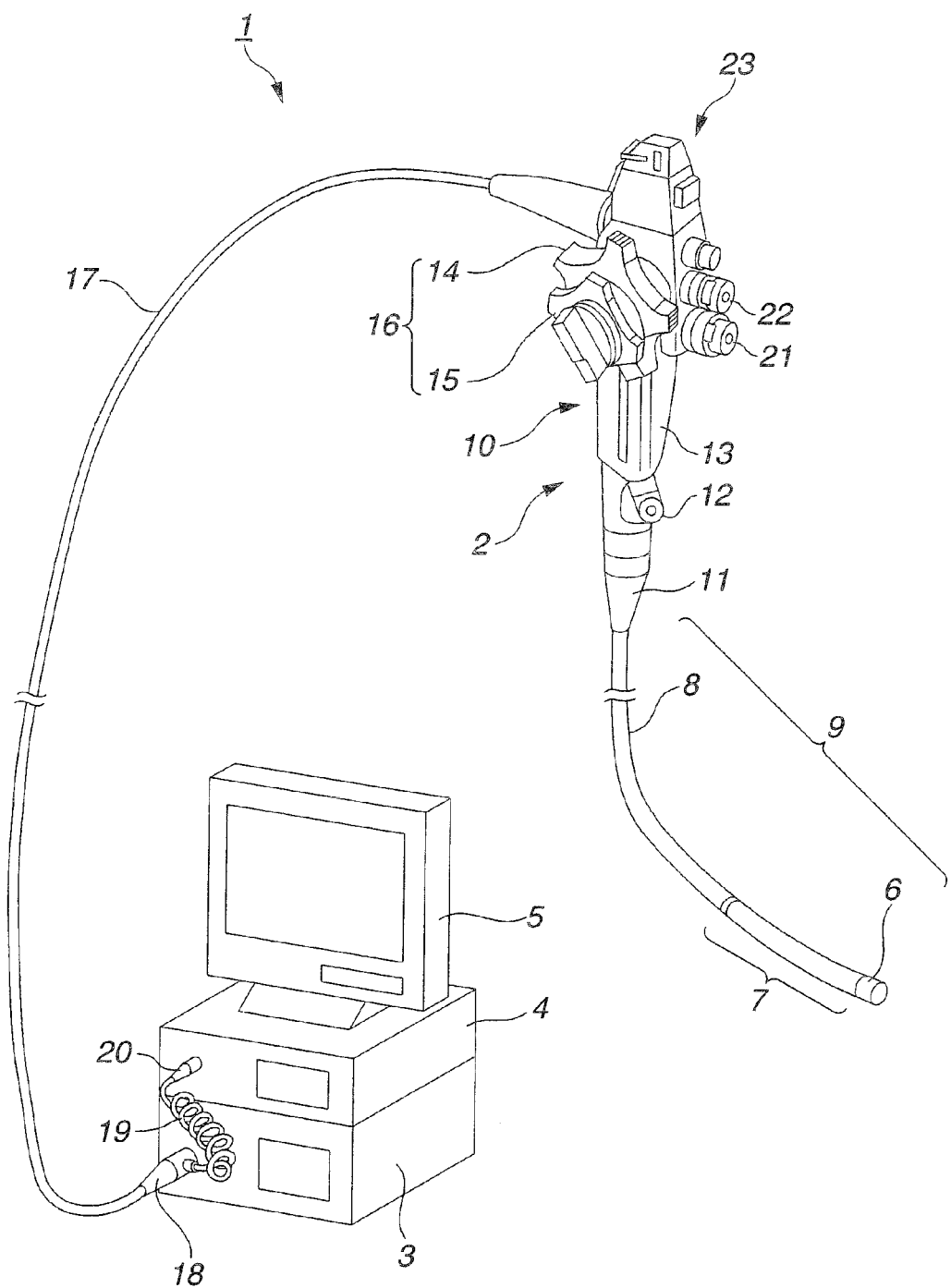
FIG. 1 is a configuration diagram showing an entire electronic endoscope system according to a first embodiment of the present invention.
Figure 2:
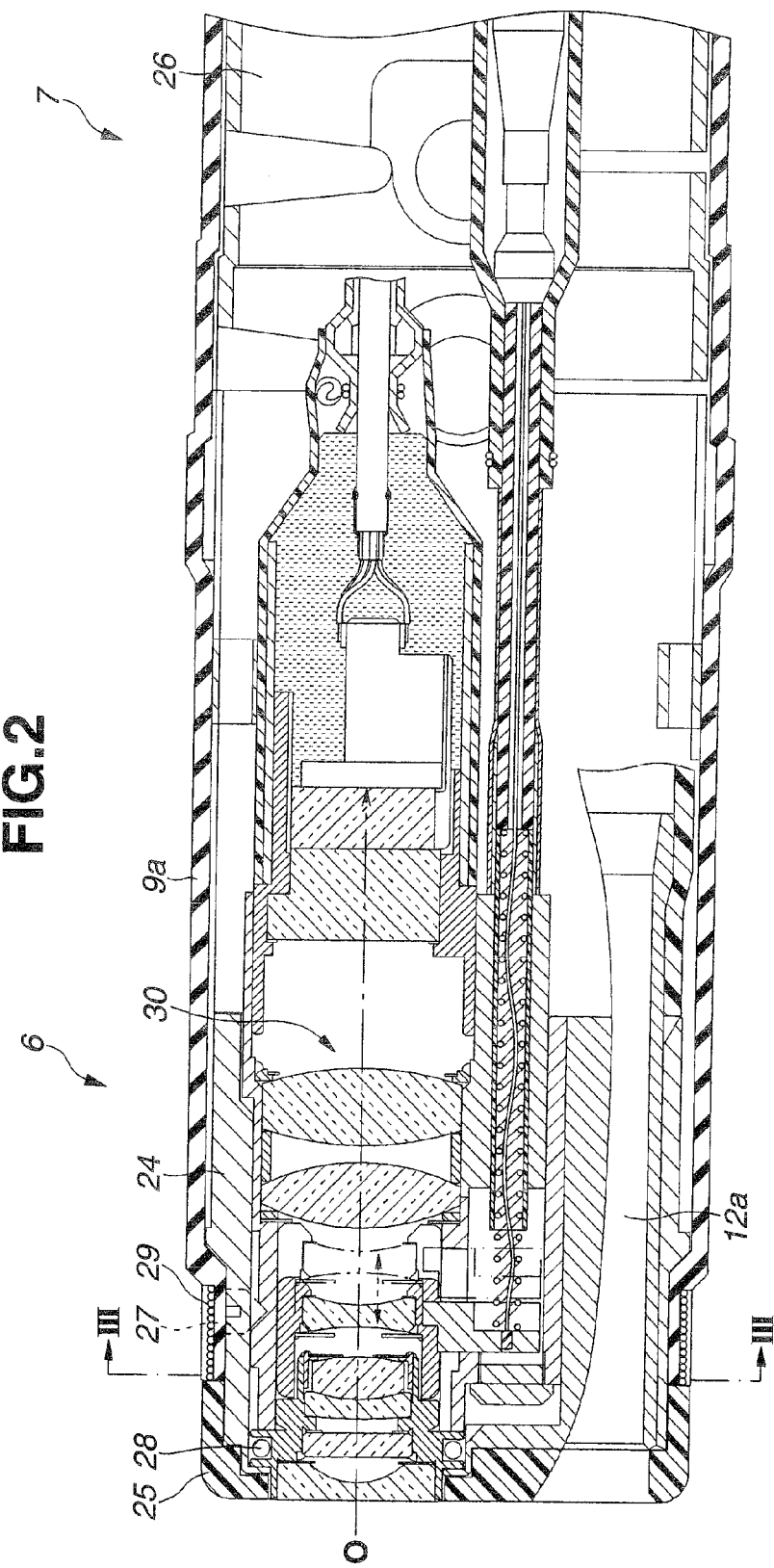
FIG. 2 is a sectional view showing the internal configuration of a distal end portion of an endoscope according to the first embodiment.
Figure 3:
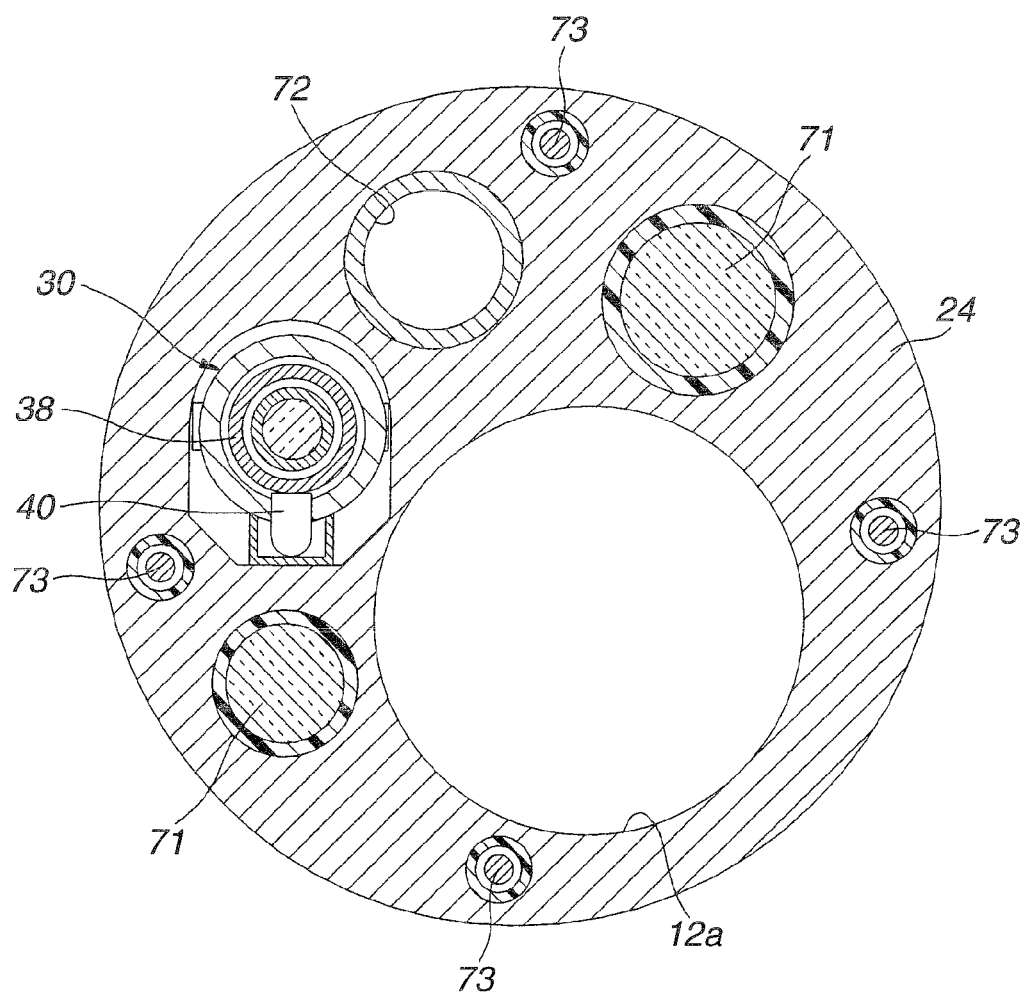
FIG. 3 is a sectional view along line III-III in FIG. 2 according to the first embodiment.
Figure 4:
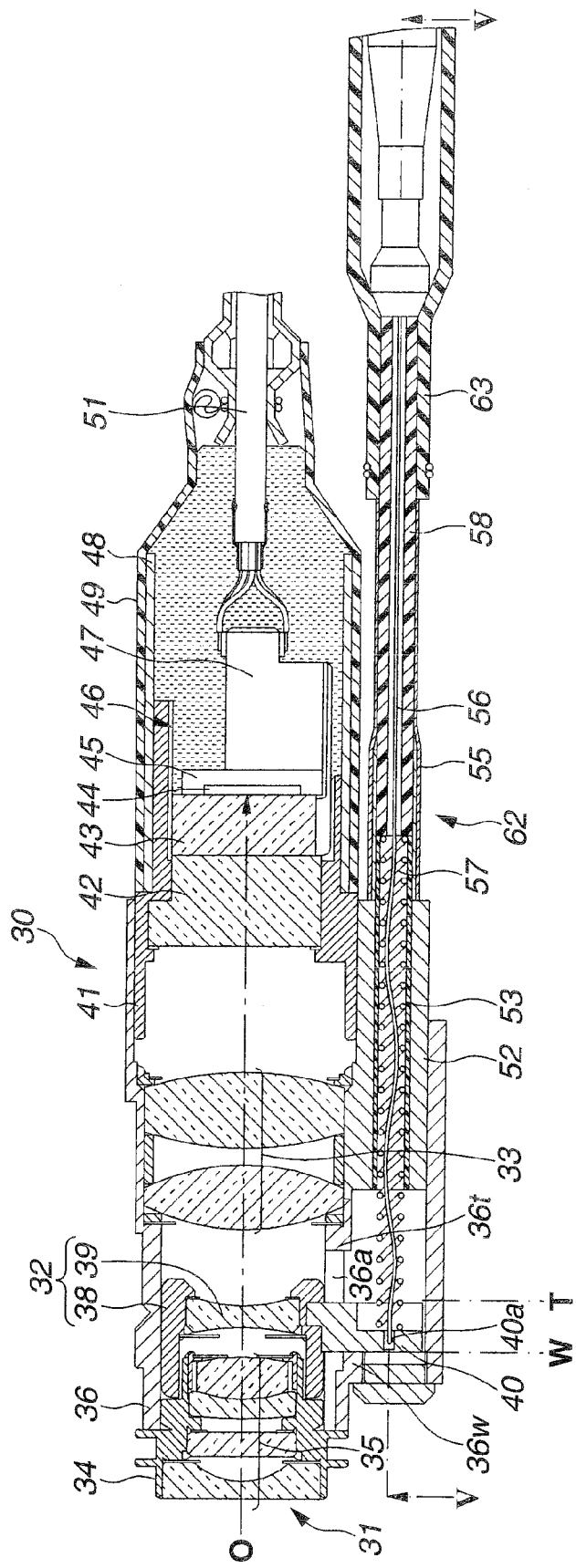
FIG. 4 is a sectional view showing the configuration of an image pickup unit according to the first embodiment.
Figure 5:
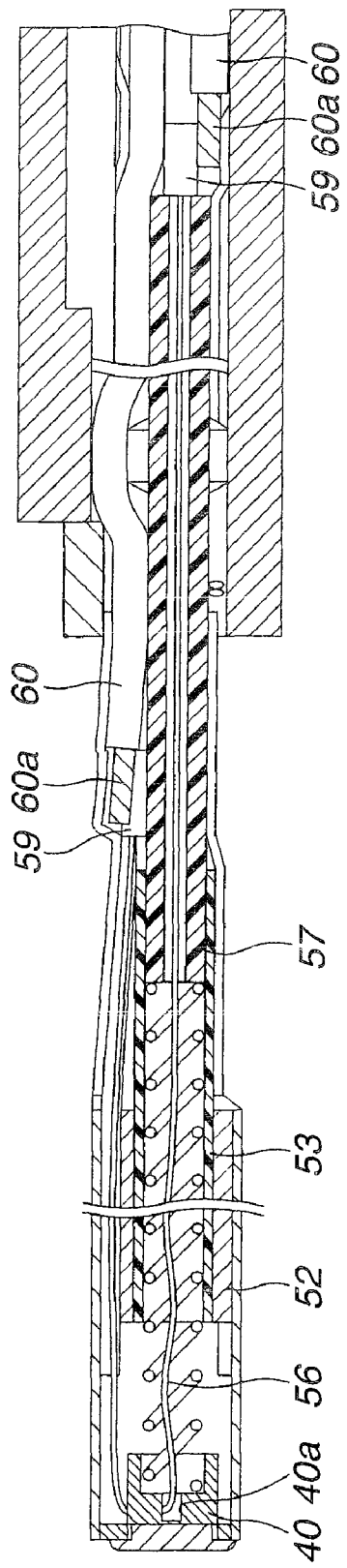
FIG. 5 is a sectional view along line V-V in FIG. 4 according to the first embodiment.
Figure 6:
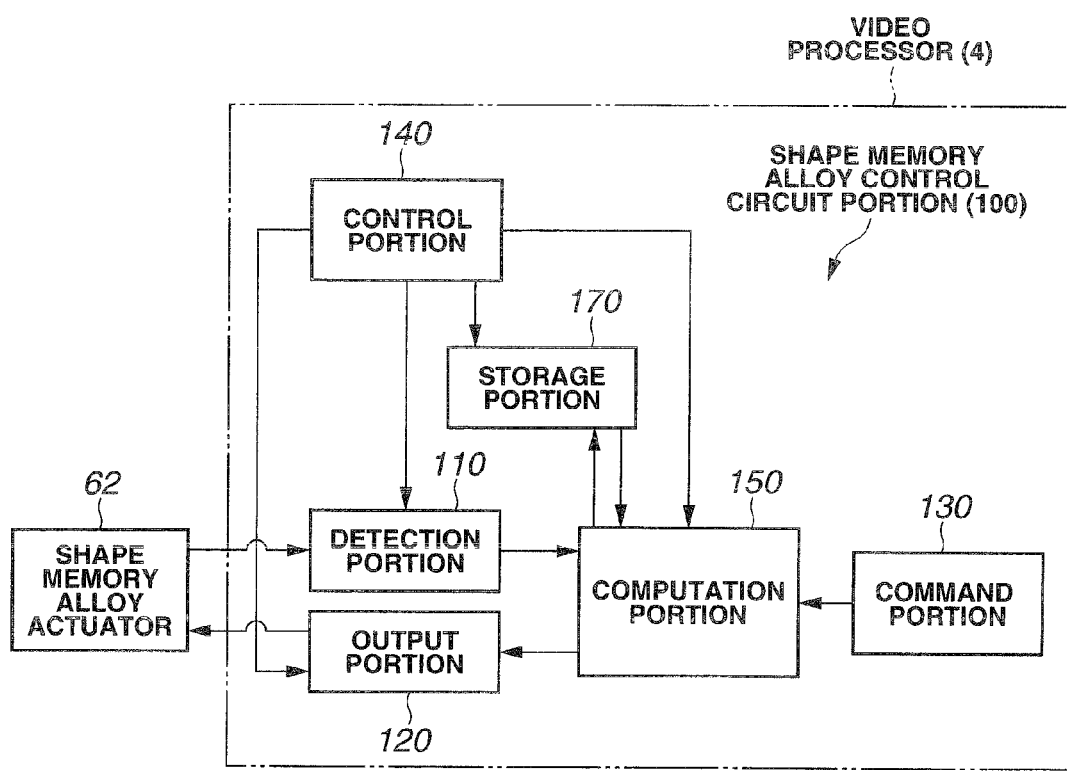
FIG. 6 is a block diagram showing a resistance feedback circuit inside a video processor that executes drive control of a shape memory alloy actuator according to the first embodiment.
Figure 7:
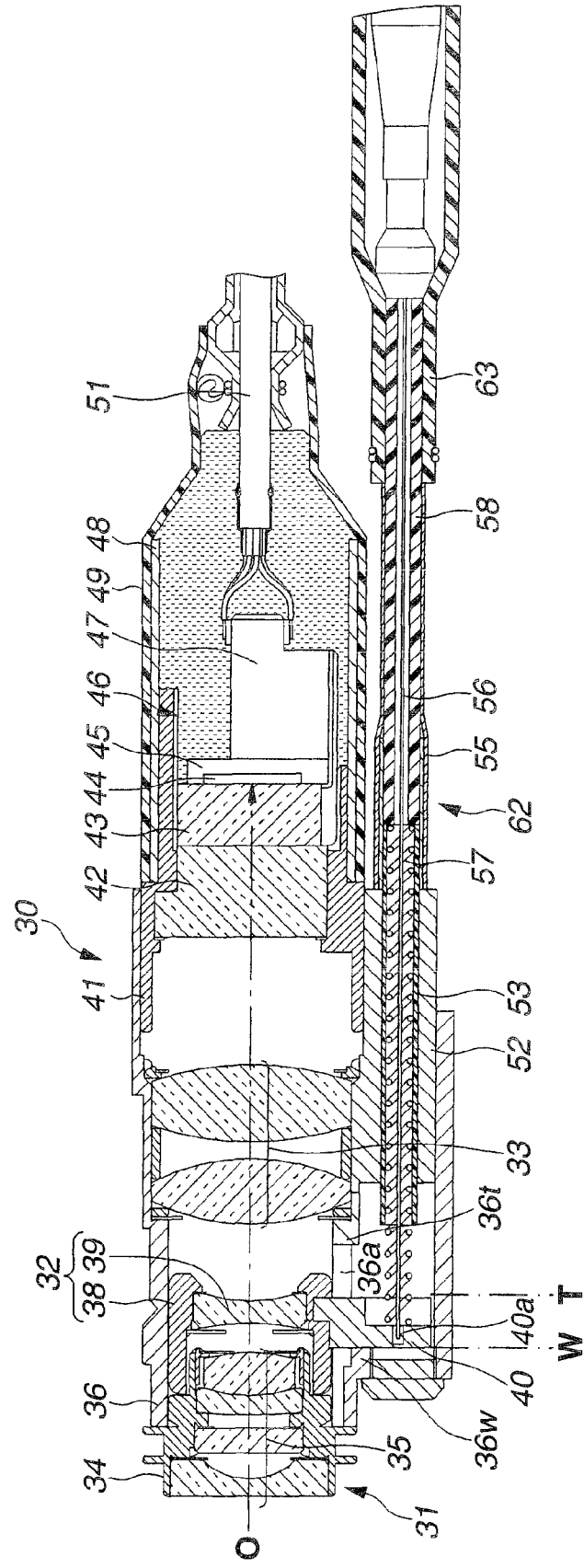
FIG. 7 is a sectional view of an image pickup unit in which a movable lens frame is in an initial state at a wide end position according to the first embodiment.
Figure 8:
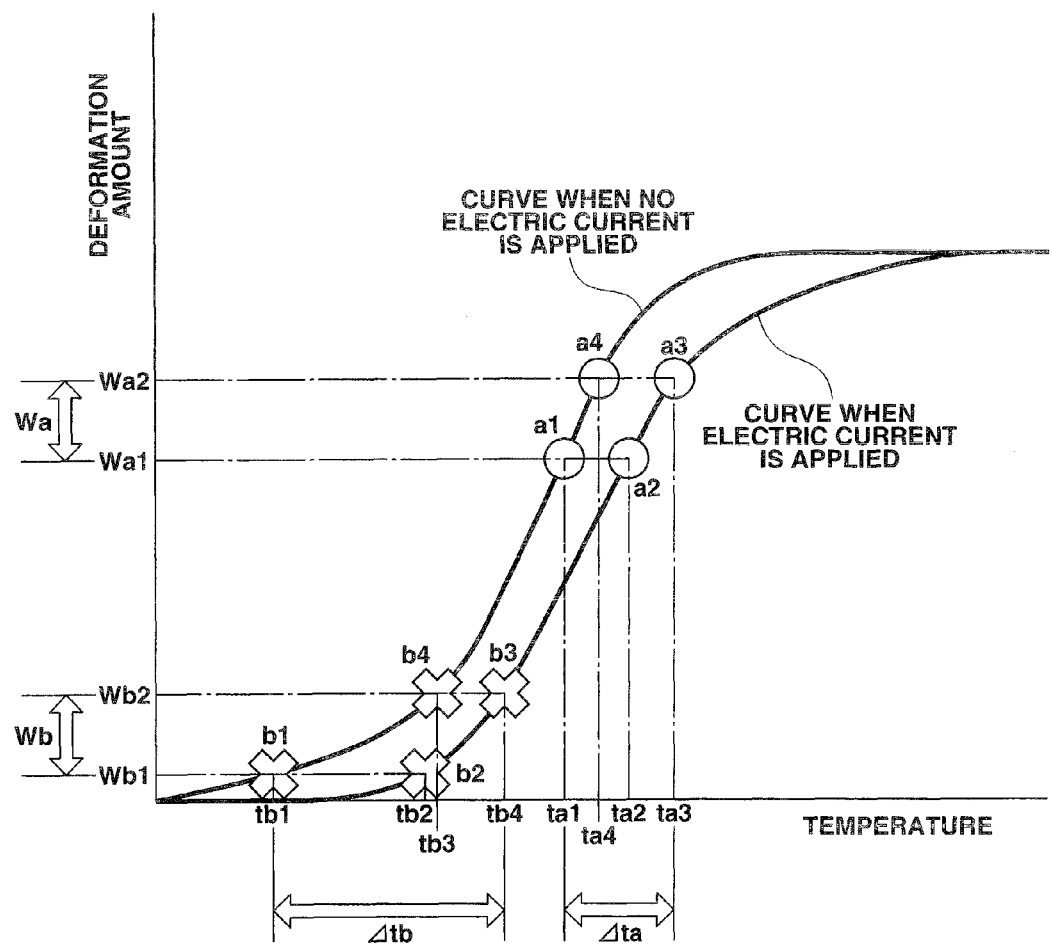
FIG. 8 is a curve graph that illustrates the relationship between deformation and temperature of a shape memory alloy wire according to the first embodiment.
Figure 9:
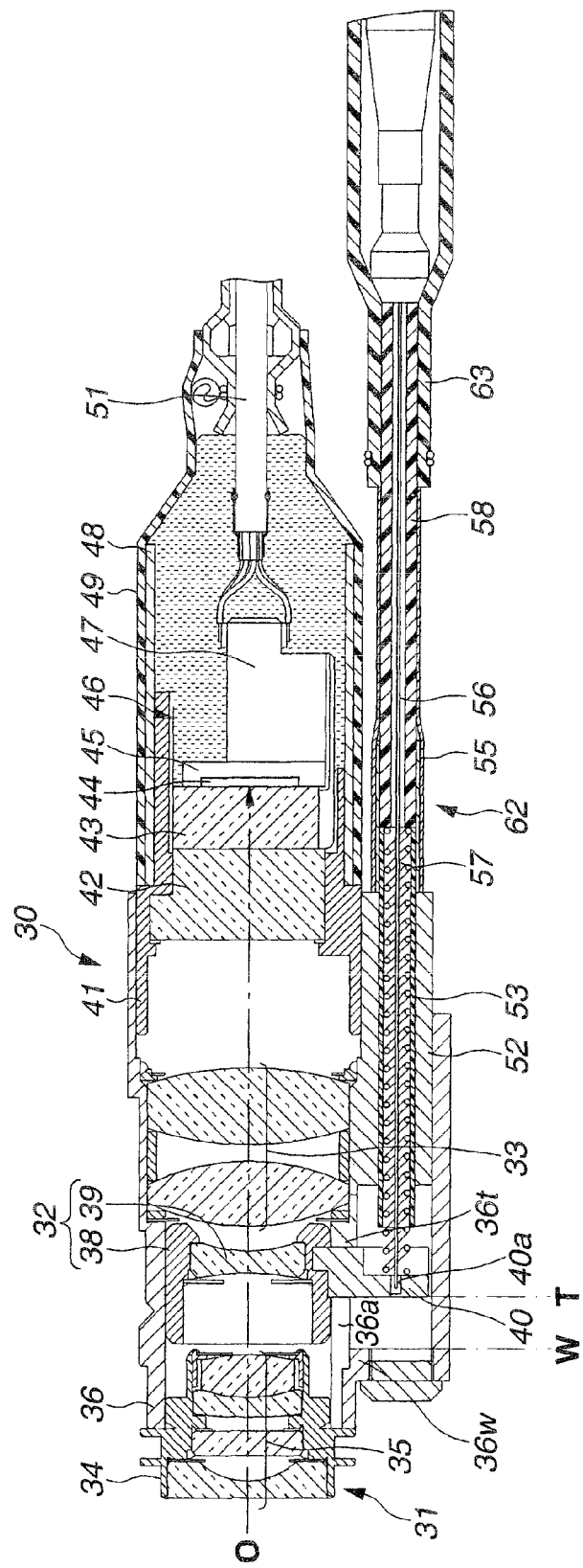
FIG. 9 is a sectional view of an image pickup unit for describing an action whereby a movable lens frame moves to a telescopic end position according to the first embodiment.
Figure 10:
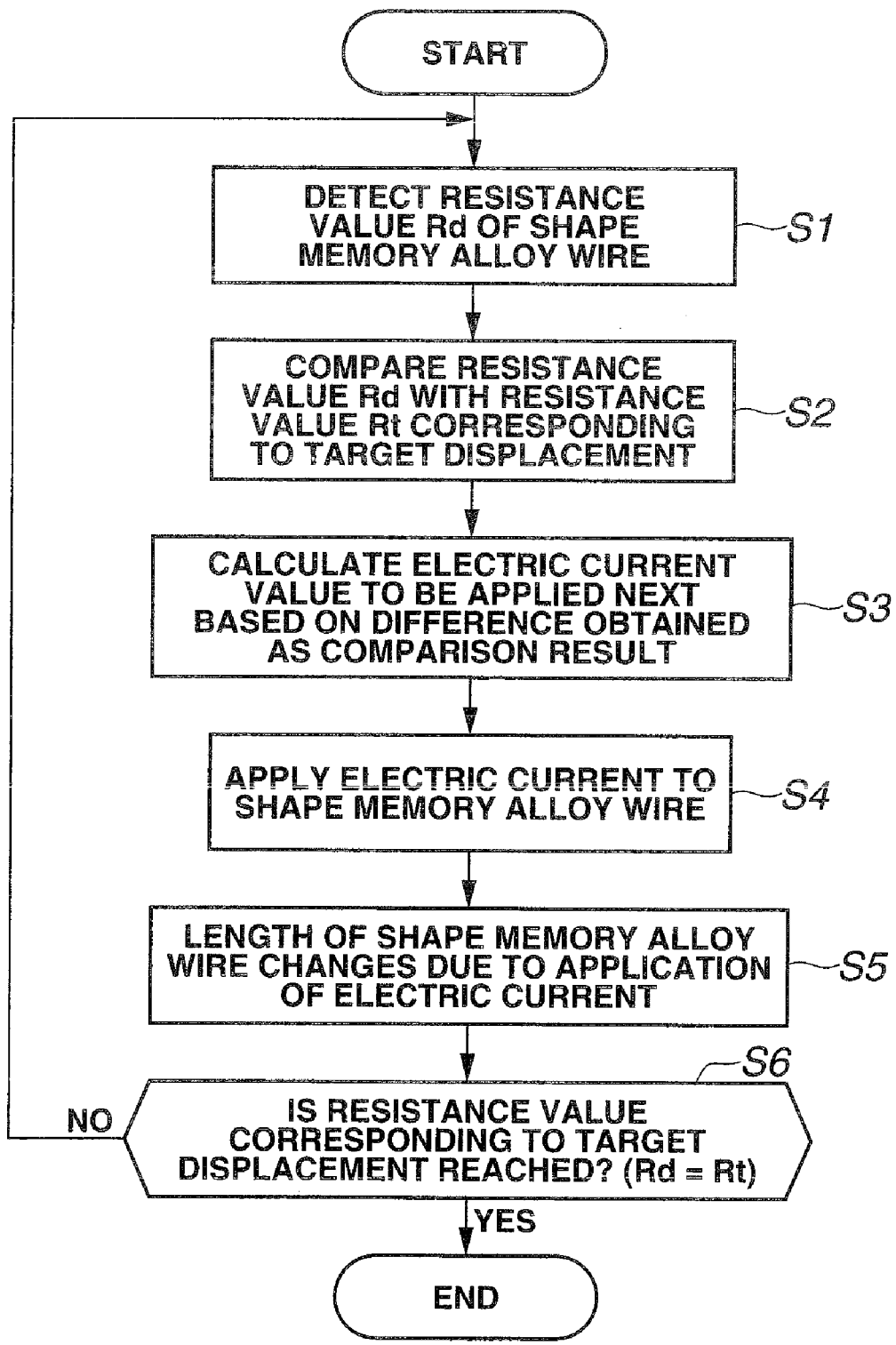
FIG. 10 is a flowchart illustrating an example of resistance value control for expanding or contracting to a target displacement an SMA wire 56 whose length is displaced in accordance with a temperature according to the first embodiment.

First, the present invention is described using FIG. 1 to FIG. 10. FIG. 1 to FIG. 10 relate to the first embodiment of the present invention. FIG. 1 is a configuration diagram showing an entire electronic endoscope system. FIG. 2 is a sectional view showing the internal configuration of a distal end portion of an endoscope. FIG. 3 is a sectional view along line III-III in FIG. 2. FIG. 4 is a sectional view showing the configuration of an image pickup unit. FIG. 5 is a sectional view along line V-V in FIG. 4. FIG. 6 is a block diagram showing a resistance feedback circuit inside a video processor that performs drive control of a shape memory alloy actuator. FIG. 7 is a sectional view of an image pickup unit in which a movable lens frame is in an initial state at a wide end position. FIG. 8 is a curve graph that illustrates the relationship between deformation and temperature of a shape memory alloy wire. FIG. 9 is a sectional view of an image pickup unit for describing an action whereby a movable lens frame moves to a telescopic end position. FIG. 10 is a flowchart illustrating a control example of resistance value control for expanding or contracting to a target displacement an SMA wire 56 whose length is displaced according to the temperature thereof.

As shown in FIG. 1, an electronic endoscope system (hereunder, referred to simply as "endoscope system") 1 of the present embodiment includes an electronic endoscope apparatus (hereunder, referred to simply as "endoscope") 2, a light source 3, a video processor 4, and a color monitor 5 that are electrically connected.

The endoscope 2 has an insertion portion 9 and an operation portion 10 from which the insertion portion 9 extends. A universal cord 17 extending from the operation portion 10 is connected to the light source 3 via a scope connector 18. A coil-shaped scope cable 19 extends from the scope connector 18. An electrical connector portion 20 is provided at another end of the scope cable 19. The electrical connector portion 20 is connected to the video processor 4.

The insertion portion 9 includes, in order from the distal end thereof, a distal end portion 6, a bending portion 7, and a flexible tube portion 8 that are provided in a linked condition. A distal end opening portion, an observation window, a plurality of illumination windows, an observation window cleaning opening, and an observation object cleaning opening, all of which are unshown in the drawings, are provided at the distal end face of the distal end portion 6.

On the rear face side of the observation window is disposed an image pickup unit, described later, that is contained inside the distal end portion 6. Further, a light guide bundle 71 (see FIG. 3) is provided at the rear face side of the plurality of illumination windows. The light guide bundle passes through the inside of the universal cord 17 from the distal end portion 6 to transmit an illumination light from the light source 3.

Unshown observation window cleaning nozzles are provided at the distal end portion 6. The observation window cleaning nozzles constitute opening portions of unshown cleaning tubes that are passed through the inside of the universal cord 17 from the distal end portion 6. These cleaning tubes are connected on the light source 3 side to an unshown cleaning tank in which cleaning water is stored and an unshown compressor.

The operation portion 10 includes a bend preventing portion 11 from which the insertion portion 9 extends, a forceps opening 12 that is provided at a side portion on the lower side, an operation portion main body 13 that constitutes a grip portion at a midway portion, a bending operation portion 16 including two bending operation knobs 14 and 15 provided on the upper side, an air supply/water supply control portion 21, a suction control portion 22, and a switch portion 23 including a plurality of switches that mainly operate image pickup functions (for example, a zooming function). In this connection, the forceps opening 12 of the operation portion 10 constitutes one opening portion of an unshown treatment instrument channel that is passed through mainly the inside of the insertion portion 9 as far as the distal end opening portion of the distal end portion 6.

Next, the configuration of the distal end portion 6 of the endoscope 2 is mainly described using FIG. 2 to FIG. 6.

As shown in FIG. 2, an image pickup unit 30 is provided inside the distal end portion 6. The image pickup unit 30 is insertedly arranged in a hard distal end rigid member 24, and is fixed to the distal end rigid member 24 with a set screw 27 from the side surface direction. An O-ring 28 for ensuring watertightness is disposed on the outer circumferential portion of the distal end side of the image pickup unit 30. A distal end cover 25 forming the distal end face of the distal end portion 6 is adhesively fixed so as to cover the distal end portion of the distal end rigid member 24.

In this connection, as described above, the distal end opening portion that is a hole formed in the distal end cover 25 constitutes an opening portion of the treatment instrument channel 12a inside the distal end portion 6. Further, a distal end insertion portion covering member 9a that is made of rubber is provided that integrally covers the outer circumference of the distal end rigid member 24 and a bending piece 26 inside the bending portion 7 so as to form the outside of the distal end portion 6 and the bending portion 7. The distal end outer circumferential portion of the distal end insertion portion covering member 9a is fixed to the distal end portion 6 by a bobbin winder adhesive portion 29.

As shown in FIG. 3, in addition to the image pickup unit 30 and the treatment instrument channel 12a, the distal end rigid member 24 is also provided with the light guide bundle 71 that guides an illumination light, the above described observation window cleaning nozzles and a conduit 72 that communicates to a cleaning tube for cleaning an observation window or the like of the distal end portion 6 or supplying air to inside a body cavity, and an angle wire 73 for performing a bending operation of the bending portion 7.

In this connection, since members such as the observation window cleaning nozzles, the cleaning tube, the light guide bundle 71, and the angle wire 73 have configurations that are known, a detailed description of those members is omitted here.

Next, the configuration of the image pickup unit 30 as illustrated in FIG. 4 and FIG. 5 is described in detail.

The image pickup unit 30 of the present embodiment has a configuration in which an internal lens moves forward and rearward to implement a zooming function or a focusing function that adjusts a focus by varying an optical property by changing the focal length. For the present embodiment, in the following description a zooming function that switches between a wide position and a telescopic position is described as a configuration in which an internal lens moves forward and backward to change a focal length and vary the optical magnification.

As shown in FIG. 4, the image pickup unit 30 principally includes, in order from the distal end thereof, a front group lens frame 34 as a fixed lens frame that retains front group lenses 35 that include a plurality of objective lenses and which is included in a front group lens unit 31, a rear group lens frame 36 as a fixed lens frame that retains rear group lenses 33 that include a plurality of objective lenses, a movable lens frame 38 that is disposed between the lens groups 35 and 33 and which constitutes the outside of a movable lens unit 32 that is a movable body that retains a movable lens 39, and an image sensor unit 46 having a CCD or a CMOS or the like.

In the image pickup unit 30, the rear end portion of the front group lens frame 34 and the front end portion of the rear group lens frame 36 are joined by fitting the two portions together. A front end portion of an image sensor retention frame 41 that retains the image sensor unit 46 is insertedly fixed in the rear end portion of the rear group lens frame 36.

The movable lens unit 32 is slidingly disposed along the direction of the photographing optical axis O within the rear group lens frame 36 at the rearward side of the front group lens unit 31. At the bottom of the movable lens frame 38 of the movable lens unit 32, a connection rod 40 is provided so as to extend downward. The sectional form at one end in the longitudinal direction of the connection rod 40 has a substantially arc shape (see FIG. 3). The connection rod 40 constitutes one part of the movable lens unit 32.

The image sensor unit 46 includes within the image sensor retention frame 41, in order from the distal end thereof, two optical members 42 and 43, an image sensor chip 45 in which an image area 44 is located at the front face, and a multilayer substrate 47. The image sensor chip 45 and the multilayer substrate 47 are electrically connected by an FPC.

Further, the multilayer substrate 47 is connected with a plurality of communication lines of a cable 51. The cable 51 is insertedly disposed inside the endoscope 2, and is electrically connected by the electrical connector portion 20 with the video processor 4 via the scope cable 19 and the universal cord 17.

A reinforcing frame 48 is fitted to the outer circumferential portion at the proximal end of the image sensor retention frame 41. A covering member 49 that is a heat-shrinkable pipe is provided on the outer circumference of the reinforcing frame 48 to cover as far as the distal end portion of the cable 51. In this connection, a protective agent such as an adhesive is filled into a space formed by the covering member 49 and the reinforcing frame 48 from the proximal end portion of the image sensor retention frame 41 in which the image sensor chip 45 is disposed.

Furthermore, at a rear lower portion of the rear group lens frame 36, an actuator retention portion 52 that retains an actuator 62 that is a shape memory alloy actuator apparatus that moves the movable lens unit 32 forward and backward is formed so as to protrude downward.

Next, the configuration of the actuator 62 that is attached to the image pickup unit 30 is described based on FIG. 4 and FIG. 5.

As shown in FIG. 4 and FIG. 5, the actuator 62 includes a long guide pipe 53 that is formed with an insulating member formed of a hard nonmetal that is insertedly disposed in the actuator retention portion 52 of the rear group lens frame 36, a shape memory alloy wire 56 that is inserted through the inside of the guide pipe 53, a helical compression spring 57 that is a pressure spring that constitutes an elastic member as an urging body that is externally fitted on the shape memory alloy wire 56 and whose proximal end side is insertedly disposed inside the guide pipe 53, a spring-stop pipe 58 through which the proximal end portion of the shape memory alloy wire 56 is inserted and which is composed of an insulating pipe that is inserted into a rear end portion of the guide pipe 53, and body blocks 59 that fix proximal ends of the shape memory alloy wire 56 by caulking. Further, a midway portion from the distal end of the spring-stop pipe 58 to the proximal end portion of the guide pipe 53 is covered by a cover tube 55 that is made of metal.

The shape memory alloy wire 56 (hereunder, the shape memory alloy wire is referred to as "SMA wire") is a wire with a diameter of several tens of microns that is made of a shape memory alloy (hereunder, referred to as "SMA") that contracts when heated and expands when cooled (natural cooling to ordinary temperature).

The SMA wire 56 is insertingly disposed inside the spring-stop pipe 58 and the guide pipe 53 in a slackened state, that is, a non-tension state under, for example, an ordinary temperature environment of 20 degrees in a state in which the actuator 62 is assembled. In other words, the connection rod 40 of the movable lens unit 32 is configured so that, for example, under an ordinary temperature environment of 20 degrees, only an urging force in the forward direction of the helical compression spring 57 acts thereon and a tensile force from the SMA wire 56 is not applied thereto.

The aforementioned guide pipe 53 is adhesively fixed to the actuator retention portion 52 in a condition in which a distal end position of the guide pipe 53 is disposed in alignment with the distal end face of the actuator retention portion 52. Further, the guide pipe 53 is precisely fixed to the actuator retention portion 52 so that the longitudinal axis thereof is parallel to the photographing optical axis O so as to satisfy the set optical property (optical magnitude) of the image pickup unit 30.

The SMA wire 56 that is inserted through the inside of the guide pipe 53 is folded back so as to penetrate through the connection rod 40 from a groove 40a that is formed at a central position of the connection rod 40. As shown in FIG. 5, the SMA wire 56 is folded back at the connection rod 40, and one end thereof is fixed by caulking to a block body 59 while the other end is fixed by caulking to another block body 59. An unshown insulating tube is covered over the SMA wire 56 on the folded-back side.

The helical compression spring 57 that is externally fitted to the SMA wire 56 is arranged between the connection rod 40 and the spring-stop pipe 58 inside the guide pipe 53 such that the ends thereof contact against connection rod 40 and the spring-stop pipe 58, respectively. Since the proximal end portion of the helical compression spring 57 contacts against the distal end face of the spring-stop pipe 58 that is fixed by the cover tube 55, and the distal end portion thereof contacts against the connection rod 40, the connection rod 40 is urged in the forward direction.

One of the block bodies 59 that fix the two ends of the SMA wire 56 as described above is formed in a shape that is larger than the hole diameter of the spring-stop pipe 58 and is disposed in a state of contact against the rear end face of the spring-stop pipe 58. The block body 59 is electrically connected by a solder or the like to an element wire 60a of a cable 60 on the electric current application side. The other block body 59 is electrically connected by a solder or the like to an element wire 60a of the cable 60 on a current feedback side.

A connecting portion between the block bodies 59 and the electric cable 60 is covered by an insulating tube 63 that integrally covers the proximal end portion of the guide pipe 53, so that the connecting portion is kept in an insulated state. In this connection, the cable 60 is disposed as far as the scope connector 18 of the universal cord 17 of the endoscope 2, and an electric current applied to the cable 60 is supplied from the video processor 4 via the scope cable 19.

Further, a notch portion 36a that constitutes a guide groove is formed in the rear group lens frame 36 so that the connection rod 40 that is connected to the movable lens unit 32 at a front lower side can move forward and backward. The rear group lens frame 36 has, at the front and rear ends forming the notch portion 36a, a restriction portion 36w that restricts forward movement of the movable lens unit 32 and, in this case, defines a wide end position W based on a front end face of the connection rod 40, and a restriction portion 36t that restricts backward movement of the movable lens unit 32 and, in this case, defines a telescopic end position T based on the front end face of the connection rod 40.

That is, forward movement of the movable lens unit 32 is restricted by the front end face of the connection rod 40 contacting against the rear end face of the restriction portion 36w. In this case, an optical property (optical magnitude) is set so that the viewing angle of the image pickup unit 30 produced by the objective lenses is a predetermined wide angle. In contrast, backward movement of the movable lens unit 32 is restricted by the rear face of the connection rod 40 contacting against the front end face of the restriction portion 36t. In this case, the optical property (optical magnitude) is set so that the viewing angle of the image pickup unit 30 produced by the objective lenses is a predetermined telescopic angle.

A resistance feedback circuit implemented by a shape memory alloy resistance control circuit portion that is provided inside the video processor 4 that executes driving control of the actuator 62 will now be described based on FIG. 6.

As shown in FIG. 6, a shape memory alloy resistance control circuit portion 100 provided inside the video processor 4 principally includes a resistance feedback circuit including a detection portion 110, an output portion 120, a command portion 130, a control portion 140, a computation portion 150, and a storage portion 170.

The detection portion 110 detects a resistance of the SMA wire 56 inside the actuator 62. The output portion 120 inputs power to the SMA wire 56 inside the actuator 62. The detection portion 110 and the output portion 120 are connected to the actuator 62.

The command portion 130 outputs a command target value to the computation portion 150. The computation portion 150 compares the command target value with a resistance value of the SMA wire 56 that is detected by the detection portion 110 to execute resistance feedback control that applies the optimal power.

When the control portion 140 outputs a command to calculate and store a resistance feedback gain to the detection portion 110, output portion 120, and computation portion 150, the computation portion 150 temporarily stops the resistance feedback control, and performs the following operation to execute calculation and storage of the resistance feedback gain. That is, based on two resistance values R1 and R2 detected for the SMA wire 56 in a predetermined time $\Delta t$, calculation of a differential resistance $\Delta R$ ($=|R2-R1|$) between the two resistance values R1 and R2 and calculation of the predetermined time $\Delta t$ and the like is performed by a gain setting portion inside the computation portion 150, and the differential resistance value $\Delta R$ and the predetermined time $\Delta t$ are outputted.

Based on the differential resistance value $\Delta R$ and predetermined time $\Delta t$ that are inputted, the gain setting portion of the computation portion 150 calculates a ratio of the two values, estimates the optimal feedback gain based on the ratio, and outputs the optimal feedback gain to the storage portion 170.

The storage portion 170 stores the inputted optimal feedback gain, and outputs the optimal feedback gain to the computation portion 150. The computation portion 150 performs resistance feedback control driving using the optimal feedback gain that is inputted.

Next, operations in which the movable lens unit 32 is moved forward or backward by the actuator 62 of the image pickup unit 30 of the present embodiment configured as described above are described in detail based on FIG. 7 to FIG. 10.

First, when power of an external device such as the light source 3 or the video processor 4 is turned on, power is inputted to the actuator 62 of the image pickup unit 30 of the endoscope 2 from the shape memory alloy resistance control circuit portion 100 of the video processor 4. At this time, an electric current at a predetermined current value is applied to the SMA wire 56 of the actuator 62. The predetermined current value is calculated by the aforementioned resistance feedback control so that an electric current of a predetermined ampere amount (number) is applied to the SMA wire 56.

As shown in FIG. 7, the term "predetermined current value" refers to an electric current value of a predetermined ampere amount (number) that is calculated as an ampere amount (number) of an electric current to be applied to the SMA wire 56 such that the SMA wire 56 that is slackened inside the actuator 62 enters a contracted state to form a rectilinear shape without the movable lens unit 32 that is being urged forward by the helical compression spring 57 moving from the wide end position W that is based on the front end face of the connection rod 40.

More specifically, the state is one in which an urging force of the helical compression spring 57 that urges the connection rod 40 of the movable lens unit 32 forward is the same as a pulling force that pulls the connection rod 40 when the SMA wire 56 contracts due to a temperature increase of the SMA wire 56 when an electric current of a predetermined ampere amount (number) is applied thereto, or preferably the urging force is stronger than the pulling force.

In this connection, if the state is one in which the urging force of the helical compression spring 57 is stronger than the pulling force of the SMA wire 56, the movable lens unit 32 is reliably urged to the wide end position W that is based on the front end face of the connection rod 40 by the helical compression spring 57.

Thus, in the endoscope 2 of the present embodiment, a state in which the SMA wire 56 is rectilinearly contracted without the movable lens unit 32 of the image pickup unit 30 moving from the wide end position W that is based on the front end face of the connection rod 40 is an initial state and a wide state.

In this connection, as shown in the curve graph of FIG. 8, an expansion/contraction state varies according to two curve relationships that represent deformation amounts by which the SMA wire 56 contracts with respect to a temperature increase produced by an applied electric current. These two curve relationships are represented by a curve with a so-called hysteresis curve shape at the time of electric current application and a curve when an electric current is not applied.

That is, the initial state of the endoscope 2 (a wide state in which the movable lens unit 32 is at the wide end position based on the front end face of the connection rod 40) is represented by a position denoted by reference characters a2 on the curve at the time of electric current application in FIG. 8. More specifically, by shrinking to a deformation amount Wa1 upon application of an electric current of a predetermined ampere amount (number) that causes the slackened SMA wire 56 to reach a temperature ta2, the SMA wire 56 is contracted to a predetermined length in a rectilinear shape (in this case, the state is one in which the aforementioned urging force is stronger than the aforementioned pulling force).

The endoscope 2 remains in this wide state as long as a predetermined switch operation is not performed using the operation portion 10 of the endoscope 2 to switch the image pickup unit 30 from the wide state to carry out telescopic zooming to the subject as described hereafter. At this time, the actuator 62 is controlled between the position denoted by reference characters a2 on the curve at the time of electric current application and a position denoted by reference characters a1 on the curve at the time of non-application of the electric current as shown in FIG. 8 by means of resistance feedback control to the actuator 62 by the shape memory alloy resistance control circuit portion 100 of the video processor 4.

That is, the shape memory alloy resistance control circuit portion 100 of the video processor 4 calculates an electric current of a predetermined ampere amount (number) to be applied to the SMA wire 56 by resistance feedback control so that the SMA wire 56 of the actuator 62 is maintained between temperatures ta1 and ta2 that are higher than the aforementioned ordinary temperature, and maintains the image pickup unit 30 of the endoscope 2 in a wide state by controlling application and stopping of the electric current.

Subsequently, to drive the actuator 62 to cause the image pickup unit 30 to perform telescopic zooming to the subject from the wide state, the user performs a predetermined switch operation using the operation portion 10 of the endoscope 2. Thereupon, by means of the aforementioned resistance feedback control driving, an electric current of a current value {ampere amount (number)} that is greater than the predetermined current value is applied to the SMA wire 56 via the cable 60 from the power supply portion of the shape memory alloy resistance control circuit portion 100 of the video processor 4.

The SMA wire 56 then generates heat by its own electrical resistance and contracts further. Thereupon, the SMA wire 56 pulls the entire movable lens unit 32 rearward via the connection rod 40 against the urging force of the helical compression spring 57 whose front end portion is contacting against the connection rod 40. As a result, the movable lens unit 32 moves rearward while the connection rod 40 is being guided in a straight line by the notch portion 36a of the rear group lens frame 36.

Thus, as shown in FIG. 9, the rearward movement of the movable lens unit 32 is restricted and stopped by the rear end face of the connection rod 40 butting against the front end face of the restriction portion 36t. In this case, the movable lens unit 32 moves as far as the telescopic end position T that is based on the front end face of the connection rod 40. In this manner, in the endoscope 2, the image pickup unit 30 is switched from a wide zooming state to a telescopic zooming state.

Thus, in the image pickup unit 30 of the endoscope 2, a state in which the movable lens unit 32 moves to the telescopic end position T that is based on the front end face of the connection rod 40 is represented by a position denoted by reference characters a3 on the curve at the time of electric current application in FIG. 8. More specifically, an electric current of a predetermined ampere amount (number) that causes the SMA wire 56 to reach a temperature ta3 is applied thereto, and the SMA wire 56 contracts the length of a deformation amount Wa (=Wa2−Wa1) against the urging force of the helical compression spring 57.

At this time, it is favorable to set the temperature so that a predetermined length that the SMA wire 56 contracts is slightly longer than a distance that the movable lens unit 32 moves to the telescopic end position T from the wide end position W based on the front end face of the connection rod 40. By setting the temperature in this way, the movable lens unit 32 can be reliably pulled to the telescopic end position T based on the front end face of the connection rod 40.

Further, the endoscope 2 remains in the telescopic state as long as the user does not perform a predetermined switch operation using the operation portion 10 of the endoscope 2 to switch the image pickup unit 30 from the telescopic state to perform wide zooming to the subject as described hereafter. At this time, the actuator 62 is controlled between the position denoted by reference characters a3 on the curve at the time of electric current application and the position denoted by reference characters a4 on the curve at the time of non-application of an electric current shown in FIG. 8 by means of resistance feedback control to the actuator 62 by the shape memory alloy resistance control circuit portion 100 of the video processor 4.

That is, the shape memory alloy resistance control circuit portion 100 of the video processor 4 calculates an electric current of a predetermined ampere amount (number) to be applied to the SMA wire 56 by resistance feedback control so that the SMA wire 56 of the actuator 62 is maintained between temperatures ta4 and ta3 that are higher than the aforementioned ordinary temperature. The shape memory alloy resistance control circuit portion 100 maintains the image pickup unit 30 of the endoscope 2 in the telescopic state by controlling application and stopping of the electric current.

Next, to drive the actuator 62 to cause the image pickup unit 30 to perform wide zooming to a subject from the telescopic state, the user performs a predetermined switch operation using the operation portion 10 of the endoscope 2. At this time, the application of an electric current to the SMA wire 56 via the cable 60 from the power supply portion of the shape memory alloy resistance control circuit portion 100 inside the video processor 4 is stopped. Thereupon, heat generation of the SMA wire 56 produced by its own resistance is stopped, the SMA wire 56 is naturally cooled, and the contracting force no longer acts.

Thereupon, the urging force of the helical compression spring 57 becomes stronger than the pulling force of the SMA wire 56 so that the movable lens unit 32 is urged forward by the helical compression spring 57 via the connection rod 40. At this time, the movable lens unit 32 moves forward while the connection rod 40 is being guided in a straight line by the notch portion 36a of the rear group lens frame 36.

In such case, as shown in FIG. 7, the forward movement of the movable lens unit 32 is restricted and stopped by the front end face of the connection rod 40 butting against the front end face of the restriction portion 36t. In this case, the movable lens unit 32 moves as far as the wide end position W based on the front end face of the connection rod 40. Thus, the image pickup unit 30 of the endoscope 2 is switched from telescopic to wide zooming.

Accordingly, in the image pickup unit 30 of the endoscope 2, a state in which the movable lens unit 32 moves to the wide end position W that is based on the front end face of the connection rod 40, similarly to the aforementioned initial state, is represented by a position denoted by reference characters a1 on the curve at the time of non-application of an electric current in FIG. 8. More specifically, by application of an electric current of a predetermined ampere amount (number) that causes the SMA wire 56 that has been slack to reach a temperature ta1, the SMA wire 56 enters a state of contraction to a predetermined length in a rectilinear shape that is a state in which the SMA wire 56 is contracted to deformation amount Wa1 (in this case also, the state is one in which the aforementioned urging force is stronger than the aforementioned pulling force).

Further, as described above, the endoscope 2 remains in the wide state as long as a predetermined switch operation is not performed using the operation portion 10 of the endoscope 2 to switch the image pickup unit 30 from the wide state to perform telescopic zooming to the subject. That is, the shape memory alloy resistance control circuit portion 100 of the video processor 4 performs control such that the SMA wire 56 of the actuator 62 is maintained between temperatures ta1 and ta2 that are higher than the aforementioned ordinary temperature, and calculates an electric current of a predetermined ampere amount (number) to be applied to the SMA wire 56 by resistance feedback control so that the image pickup unit 30 of the endoscope 2 is maintained in the wide state by controlling application and stopping of the aforementioned electric current.

An example will now be described of control by the shape memory alloy resistance control circuit portion 100 of resistance value control for expanding/contracting to a target displacement the SMA wire 56 whose length changes in accordance with a temperature as described above, based on the block diagram shown in FIG. 6 and the flowchart shown in FIG. 10.

When expanding the SMA wire 56 to a target displacement, first, the control portion 140 provided in the shape memory alloy resistance control circuit portion 100 of the video processor 4 executes control to detect the present resistance value Rd of the SMA wire 56 using the detection portion 110 (S1). Next, based on a command from the command portion 130, the control portion 140 executes control to compare a resistance value Rt corresponding to a target displacement that is stored in the storage portion 170 with the detected resistance value Rd using the computation portion 150 (S2). In this connection, the resistance value Rt corresponding to the target displacement is a value that is previously set based on the specifications of the SMA wire 56.

The control portion 140 then controls to cause the computation portion 150 to calculate an electric current value {ampere amount (number)} to be applied next based on the difference between the resistance value Rd and the resistance value Rt that is the comparison result of the computation portion 150 (S3). Subsequently, the control portion 140 controls so as to apply an electric current of the thus-calculated electric current value {ampere amount (number)} to the SMA wire 56 of the actuator 62 from a heat circuit inside the output portion 120 from the computation portion 150 (S4).

Thus, the temperature of the SMA wire 56 rises in accordance with the applied current, and the length of the SMA wire 56 changes (contracts) (S5). At this time, the control portion 140 controls to cause the detection portion 110 to detect the present resistance value Rd of the SMA wire 56, and determines whether or not the resistance value Rd has reached the resistance value Rt corresponding to the target displacement using the computation portion 150 (S6).

In step S6, if the resistance value Rd has reached the resistance value Rt corresponding to the target displacement, application of the electric current to the SMA wire 56 of the actuator 62 from the heat circuit (not shown) inside the output portion 120 is stopped and the routine ends.

In contrast, in step S6, if the resistance value Rd has not reached the resistance value Rt corresponding to the target displacement, the control portion 140 returns to step S1 again to repeat the routine from step S1 to S6.

As described above, the endoscope system 1 of the present embodiment is configured to switch the image pickup unit 30 of the endoscope 2 between a wide and a telescopic zooming function by controlling expansion of the SMA wire 56 between temperatures ta2 and ta3 that are higher than an ordinary temperature at the time of application of an electric current and between temperatures ta1 and ta4 that are higher than an ordinary temperature at the time of non-application of an electric current as shown in FIG. 8, by controlling the actuator 62 of the image pickup unit 30 using the shape memory alloy resistance control circuit portion 100 of the video processor 4.

Further, the endoscope 2 is configured to perform temperature control of the SMA wire 56 by applying or stopping application of an electric current to the SMA wire 56 between temperatures ta2 and ta3 that are higher than an ordinary temperature to maintain a wide state of the image pickup unit 30 and between temperatures ta3 and ta4 that are higher than an ordinary temperature to maintain a telescopic state of the image pickup unit 30.

According to the endoscope 2 of the present embodiment, even when heat such as the body temperature of an examinee or heat from the light guide bundle 71 that guides an illumination light is transmitted to the SMA wire 56 provided in the actuator 62 of the image pickup unit 30 and the temperature thereof rises to cause the SMA wire 56 to contract, since the SMA wire 56 is provided in a slackened state (non-tension state) when a current is not passed thereto under an ordinary temperature, as long as the contraction is within the range of the amount of slack the movable lens unit 32 of the image pickup unit 30 is not pulled rearward from the wide end position that is based on the front end face of the connection rod 40. It is thus possible to prevent an optical property of the image pickup unit 30 (in particular, the optical magnitude in the wide state) from changing against the intention of the user.

Further, with respect to the actuator 62 of the present embodiment, in order to obtain the deformation amount Wa of the SMA wire 56 for moving the movable lens unit 32 to switch between a wide and a telescopic state of the image pickup unit 30 that is performed based on control of the shape memory alloy resistance control circuit portion 100 of the video processor 4, as shown in FIG. 8, the SMA wire 56 reaches temperatures ta1 to ta4 that correspond to positions denoted by reference characters a2 and a3 on the curve at the time of electric current application and positions denoted by reference characters a1 and a4 on the curve at the time of non-application of an electric current, and a temperature change amount from the maximum temperature difference is $\Delta ta$ (=ta3−ta1).

In contrast, in a conventional image pickup unit, an SMA wire is not arranged to have slackness when a current is not passed thereto under an ordinary temperature. Therefore, as shown in FIG. 8, to obtain a deformation amount Wb of the SMA wire for moving the movable lens unit to switch between a wide state and a telescopic state, the temperatures of the SMA wire are temperatures tb1 to tb4 that correspond to positions denoted by reference characters b2 and b3 on the curve at the time of electric current application and positions denoted by reference characters b1 and b4 on the curve at the time of non-application of an electric current. Thus, the temperature change amount from the maximum temperature difference is $\Delta tb$ (tb3−tb1), which is greater than the temperature change amount $\Delta ta$ of the present embodiment ($\Delta tb > \Delta ta$). In this connection, it is assumed that the deformation amount Wa and the deformation amount Wb are the same amount (Wa=Wb).

Thus, the actuator 62 of the present embodiment can stably obtain a deformation amount Wa of the SMA wire 56 for moving the movable lens unit 32 to switch between a wide state and a telescopic state of the image pickup unit 30 by a temperature change amount $\Delta ta$ that is less than a conventional temperature change amount by using a temperature change that is at least a temperature of the SMA wire 56 at which a predetermined deformation amount can be obtained and a characteristic portion of the deformation amount.

Therefore, the actuator 62 of the present embodiment can stably move the movable lens unit 32 backward and forward to switch between a wide state and a telescopic state in the image pickup unit 30 and can quicken the expansion/contraction response speed of the SMA wire 56. As a result, the endoscope 2 can stably switch an optical property (optical magnitude) of the image pickup unit 30 between a wide and telescopic state at the desired timing of the user.

Second Embodiment

Next, the second embodiment of the present invention is described based on FIG. 11 to FIG. 14B.

FIG. 11 to FIG. 14B relate to the second embodiment of the present invention. FIG. 11 is a sectional view showing the configuration of an image pickup unit. FIGS. 12A, 12B are sectional views of the image pickup unit in an initial state in which the movable lens frame is at a wide end position. FIGS. 13A, 13B are sectional views of the image pickup unit for describing an action in which the movable lens frame moves to a telescopic end position. FIGS. 14A, 14B are sectional views of the image pickup unit that illustrate a state in which the movable lens frame has moved to the telescopic end position.

In the following description, the same reference numerals are used for components that are the same as components of the image pickup unit 30 of the endoscope system 1 of the first embodiment described above, and a detailed description thereof is omitted.

In this connection, among the conventional endoscopes that move a movable lens frame to vary optical properties, for example, as described in Japanese Patent Application Laid-Open Publication No. 11-197096, an endoscope is known that is equipped with an operation wire for moving a movable lens frame and a lens frame at a distal end portion, and in which an image pickup unit is provided with a first helical compression spring and a second helical compression spring that are disposed at a back end of the movable lens frame and that urge the movable lens frame relatively. This conventional endoscope can be configured to include an image pickup unit which enables forward and backward movement of a movable lens frame to be stably and reliably performed by means of the two helical compression springs that perform the relative urging.

However, according to such a conventional technology for an image pickup unit of an endoscope, since the two helical compression springs are disposed on the same axis sandwiching the movable lens frame as a movable body, a length in an axial direction along which the movable lens frame moves forward and backward is lengthened by the two helical compression spring and the thickness of a portion of the movable lens frame against which one end of each of the helical compression springs contacts. When an image pickup unit with such a configuration is integrated into an endoscope, the length in a direction of an insertion axis that is the longitudinal axis of a rigid distal end portion of the insertion portion increases. When the rigid portion of the insertion portion lengthens in this way, there is a problem that pain is imparted to an examinee when inserting the insertion portion into a body cavity of the examinee.

Therefore, an object of the present embodiment is to provide, in addition to the advantages of the first embodiment, a shape memory alloy actuator to be provided inside an image pickup unit of an endoscope that can stably and reliably move a movable lens frame as a movable body backward and forward inside an image pickup unit, and further, can shorten the length of a rigid portion of an insertion portion in which the image pickup unit is disposed to thereby achieve a smaller size and improve insertability into a body cavity.

First, as shown in FIG. 11, the image pickup unit 30 of the present embodiment is provided with two helical compression springs 57 and 66 that urge the connection rod 40 of the movable lens unit 32 forward and rearward relatively (the helical compression spring 57 that is a pressure spring constitutes a first elastic member and the helical compression spring 66 that is a pressure spring constitutes a second elastic member). In this connection, the SMA wire 56 is not connected to the connection rod 40 of the present embodiment, and the connection rod 40 includes a notch portion 40b that is formed at a rear face portion and a hole 40c in which a rear end portion of the helical compression spring 66 is insertingly disposed in a rearward direction at an upper part of the front face.

The SMA wire 56 of the present embodiment is provided with an anchor 65 as an indirect action member that indirectly acts on the movable lens unit 32. The anchor 65 is made of a non-metal with insulating properties and is arranged at a folded back distal end portion. The anchor 65 is not connected to the connection rod 40. The distal end of the helical compression spring 57 contacts against a rear face portion of the anchor 65 such that the anchor 65 receives the urging force of the helical compression spring 57 and contacts against the rear face of the connection rod 40 forming the notch portion 40b.

The helical compression spring 57 has the same configuration as the helical compression spring of the above described first embodiment, and is a first urging body that urges the connection rod 40 forward. The distal end of the helical compression spring 57 contacts against the rear face of the anchor 65 that is attached to the SMA wire 56, and thereby indirectly urges the connection rod 40 forward together with the anchor 65. In this connection, the helical compression spring 57 is set so that an urging force that urges the connection rod 40 forward via the anchor 65 is an urging force (spring pressing force that urges the movable lens unit 32 forward) that is several tens of times greater than an urging force from the helical compression spring 66 that urges the connection rod 40 rearward.

The helical compression spring 66 is a second urging body that urges the connection rod 40 rearward. The urging force (spring pressing force that urges the movable lens unit 32 rearward) of the helical compression spring 66 is set to be equivalent to several tens of times the weight (mass) of the movable lens unit 32. The rear end portion of the helical compression spring 66 is insertingly disposed in the hole 40c of the connection rod 40. Further, the helical compression spring 66 is arranged so that the distal end thereof contacts against an outward-flange shaped rear face portion of the front group lens frame 34 to urge the connection rod 40 rearward.

The centers of the respective helical compression springs 57 and 66 are disposed on different parallel axes a and b that are arranged so that the respective axes of the helical compression springs 57 and 66 in the expanding/contracting direction that are parallel with the optical axis O are separated from each other by a predetermined distance L. That is, in the connection rod 40, the hole 40c is formed in the rearward direction at the upper part of the front face thereof so that the center axis a for expansion and contraction of the helical compression spring 66 is separated by the predetermined distance L from the center axis b for expansion and contraction of the helical compression spring 57.

Thus, the image pickup unit 30 of the present embodiment includes two helical compression springs 57 and 66 that urge the connection rod 40 of the movable lens unit 32 forward and backward relatively. The helical compression springs 57 and 66 are arranged at positions such that the central axes a and b of the helical compression springs 57 and 66 are separated by a predetermined distance L. As a result, in the image pickup unit 30, even if the thickness of the connection rod 40 is thinned, the depth of the hole 40c of the connection rod 40 in which the rear end portion of the helical compression spring 66 that urges the movable lens unit 32 rearward is insertingly disposed can be adequately secured.

It is therefore possible to decrease the size of the image pickup unit 30, and also to shorten the length in the insertion axis direction that is the longitudinal axis direction of the rigid distal end portion 6 of the insertion portion 9 in which the image pickup unit 30 is disposed. As a result, since it is possible to shorten the length of the rigid distal end portion 6, the endoscope 2 can be made with a minimally invasive configuration that does not cause pain to an examinee when inserting the insertion portion 9 into a body cavity of the examinee.

Next, an action by the actuator 62 in the image pickup unit 30 configured as described above that causes the movable lens unit 32 to move forward and backward is described based on FIG. 8 and FIG. 11 to FIG. 14B. In the following description, a detailed description of driving control of the actuator 62 is simplified for convenience since the action is the same as the action of the actuator 62 in the first embodiment described above.

First, when the power of an external device such as the light source 3 or the video processor 4 is turned on, power is inputted to the actuator 62 of the image pickup unit 30 of the endoscope 2 from the shape memory alloy resistance control circuit portion 100 of the video processor 4, similarly to the first embodiment.

Figures 12A, 12B:
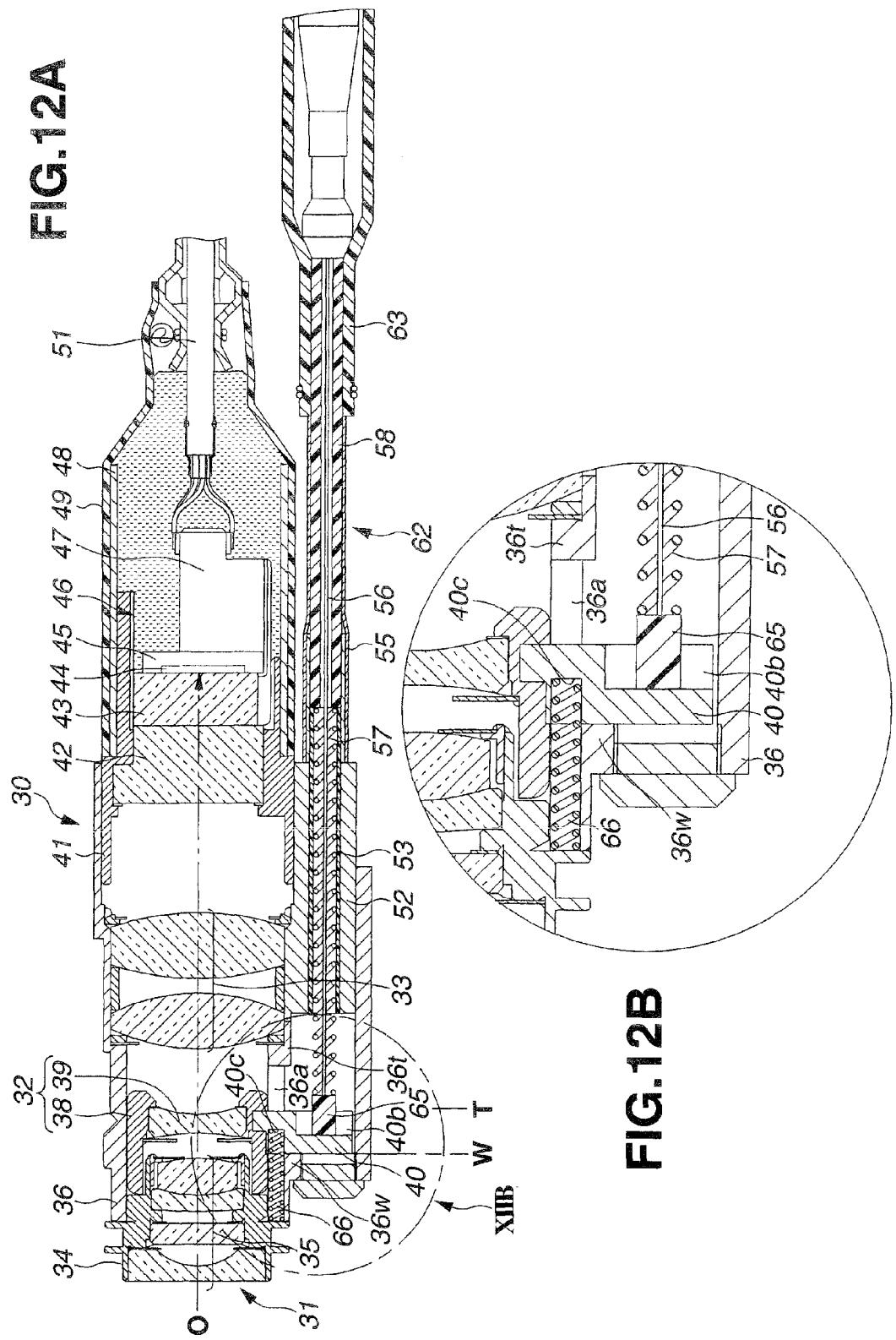
FIG. 12A is a sectional view of an image pickup unit in which a movable lens frame is in an initial state at a wide end position according to the second embodiment.
FIG. 12B is an enlarged view of a portion surrounded by a circle XIIA in FIG. 12A according to the second embodiment.

Thereupon, as shown in FIGS. 12A, 12B, the SMA wire 56 that is slackened inside the actuator 62 enters a contracted state so as to form a rectilinear shape without the movable lens unit 32 including the connection rod 40 that is urged forward by the helical compression spring 57 via the anchor 65 moving from the wide end position W that is based on the front end face of the connection rod 40.

At this time, an electric current ampere amount (number) is calculated by control of the shape memory alloy resistance control circuit portion 100 of the video processor 4 in accordance with the deformation amount of the SMA wire 56 that pulls the anchor 65 against the urging force of the helical compression spring 57 so that the movable lens unit 32 does not move from the wide end position W based on the front end face of the connection rod 40 even upon receiving an urging force towards the rearward direction of the movable lens unit 32 from the helical compression spring 66, and an electric current of the predetermined ampere amount (number) is applied to the SMA wire 56. Thus, in the endoscope 2 of the present embodiment also, a state in which the SMA wire 56 is rectilinearly contracted without the movable lens unit 32 of the image pickup unit 30 moving from the wide end position W that is based on the front end face of the connection rod 40 is the initial state and a wide state.

In this case also, as shown in the curve graph in FIG. 8, an expansion/contraction state varies according to two curve relationships that represent deformation amounts by which the SMA wire 56 contracts with respect to a temperature increase produced by an applied electric current. These two curve relationships are represented by a curve with a so-called hysteresis curve shape at the time of electric current application and a curve at the time an electric current is not applied.

That is, the initial state of the endoscope 2 (a wide state in which the movable lens unit 32 is at the wide end position based on the front end face of the connection rod 40) is represented by a position denoted by reference characters a2 on the curve at the time of electric current application in FIG. 8. More specifically, by contracting to a deformation amount Wa1 by application of an electric current of a predetermined ampere amount (number) that causes the slackened SMA wire 56 to reach a temperature ta2, the SMA wire 56 contracts to a predetermined length in a rectilinear shape.

Further, according to the present embodiment also, the endoscope 2 retains this wide state as long as a predetermined switch operation is not performed using the operation portion 10 of the endoscope 2 to switch the image pickup unit 30 from the wide state to perform telescopic zooming towards the subject.

In the endoscope 2, when the actuator 62 is driven to switch the image pickup unit 30 from the wide state to perform telescopic zooming towards the subject, an electric current of a predetermined ampere amount (number) is applied to the SMA wire 56 such that the SMA wire 56 generates heat by its own electrical resistance and contracts further. Thereupon, the SMA wire 56 pulls the anchor 65 rearward against the urging force of the helical compression spring 57 whose front end portion is contacting against the anchor 65.

In accompaniment therewith, the movable lens unit 32 moves rearward with the connection rod 40 that is being urged rearward by the urging force of the helical compression spring 66, while still contacting against the anchor 65. At this time, the movable lens unit 32 moves rearward while the connection rod 40 is being guided in a straight line by the notch portion 36a of the rear group lens frame 36.

In such case, as shown in FIGS. 13A, 13B, the rearward movement of the movable lens unit 32 is restricted and stopped by the rear end face of the connection rod 40 abutting against the front end face of the restriction portion 36t. At this time, the movable lens unit 32 moves as far as the telescopic end position T that is based on the front end face of the connection rod 40. This state is represented by a position denoted by reference characters a3 on the curve at the time of electric current application in FIG. 8. More specifically, by further contracting as far as a deformation amount Wa2 from the deformation amount Wa1 (contracting further by deformation amount Wa) due to application of an electric current of a predetermined ampere amount (number) that causes the SMA wire 56 to reach a temperature ta3, the SMA wire 56 is contracted to a predetermined length.

Further, with respect to the movable lens unit 32, as shown in FIGS. 14A, 14B, the electric current of the predetermined ampere amount (number) continues to be applied to the SMA wire 56 so as to separate the anchor 65 from the connection rod 40 against which the anchor 65 has been contacting, and thus the SMA wire 56 contracts further.

In this state, an electric current of a predetermined ampere amount (number) that causes the SMA wire 56 to reach a higher temperature than the temperature ta3 is applied to the SMA wire 56 so that the deformation amount of the SMA wire 56 becomes larger than that at the position denoted by reference characters a3 on the curve at the time of electric current application in FIG. 8. As a result, the SMA wire 56 shrinks further from the deformation amount Wa2 and enters a state in which the SMA wire 56 is contracted to a predetermined length.

Thus, the image pickup unit 30 in the endoscope 2 is switched from wide to telescopic zooming. Further, as shown in FIGS. 14A, 14B, in the image pickup unit 30, a state in which the connection rod 40 and the anchor 65 are separated from each other is set as a telescopic state. By controlling the temperature of the SMA wire 56 to cause the SMA wire 56 to contract in this manner, even if control that balances the urging forces of the helical compression springs 57 and 66 becomes erratic, the movable lens unit 32 does not receive an urging force from the helical compression spring 57 to urge the movable lens unit 32 forward, and only the rearward urging force from the helical compression spring 66 acts on the movable lens unit 32.

That is, since the movable lens unit 32 receives only a force that acts in the rearward direction without receiving a force that acts in the forward direction, the rear end face of the connection rod 40 contacts against the front end face of the restriction portion 36t that defines the telescopic end position T that is based on the front end face of the connection rod 40, and movement thereof in the rearward direction is reliably restricted.

In this connection, in the endoscope 2, in a case in which the actuator 62 of the image pickup unit 30 is driven to cause the image pickup unit 30 to perform wide zooming to a subject from a telescopic state, application of a current to the SMA wire 56 via the cable 60 from the power supply portion of the shape memory alloy resistance control circuit portion 100 inside the video processor 4 is stopped. The anchor 65 is then urged forward by the helical compression spring 57 to contact against the connection rod 40, and the movable lens unit 32 moves forward. As shown in FIGS. 12A, 12B, forward movement of the movable lens unit 32 is restricted and stopped by the front end face of the connection rod 40 contacting against the rear end face of the restriction portion 36w, and the movable lens unit 32 thus moves as far as the wide end position W that is based on the front end face of the connection rod 40. Thus, the image pickup unit 30 of the endoscope 2 is switched from telescopic zooming to wide zooming.

According to the image pickup unit 30 of the endoscope system 1 of the present embodiment described above, similarly to the advantages of the first embodiment, forward and backward movement of the movable lens unit 32 that switches between wide zooming and telescopic zooming can be stably performed and the expansion/contraction response speed of the SMA wire 56 can be quickened.

Furthermore, even though the configuration of the image pickup unit 30 of the present embodiment includes two helical compression springs 57 and 66 that act to urge the movable lens unit 32 in a relative manner, the image pickup unit 30 can be made compact, and the length in an insertion axis direction that is the longitudinal axis of the rigid distal end portion 6 of the insertion portion 9 in which the image pickup unit 30 is disposed can be shortened.

Thus, in addition to the advantages of the first embodiment, since it is possible to shorten the length of the rigid distal end portion 6, the endoscope 2 can be provided with a minimally invasive configuration that does not cause pain to an examinee when inserting the insertion portion 9 into a body cavity of the examinee.

Third Embodiment

Next, the third embodiment of the present invention is described based on FIG. 15A to FIG. 18B.

FIG. 15A to FIG. 18B relate to the third embodiment of the present invention. FIGS. 15A, 15B are sectional views illustrating the configuration of an image pickup unit. FIGS. 16A, 16B are sectional views of the image pickup unit for describing an action in which a movable lens frame moves to a telescopic end position. FIGS. 17A, 17B are sectional views of the image pickup unit that illustrate a state in which application of an electric current to an SMA wire is stopped in a state in which the movable lens frame has moved to the telescopic end position. FIGS. 18A, 18B are sectional views of the image pickup unit that illustrate a state in which an electric current is applied to the SMA wire again, in a state in which the movable lens frame has moved to the telescopic end position.

In the following description, the same reference numerals are used for components that are the same as components of the image pickup unit 30 of the endoscope system 1 of the first and second embodiments described above, and a detailed description thereof is omitted. Further, the configuration of the image pickup unit of the present embodiment as described below is substantially the same as that of the image pickup unit 30 of the second embodiment.

As shown in FIGS. 15A, 15B, in the image pickup unit 30 of the present embodiment, a magnet 75 is arranged at the restriction portion 36*t* of the rear group lens frame 36 that defines the telescopic end position T that is based on the front end face of the connection rod 40, and the connection rod 40 of the movable lens unit 32 is composed by a ferromagnetic body. The remaining configuration is the same as that of the image pickup unit 30 of the second embodiment.

The magnetic force of the magnet 75 is set such that when the front end face of the connection rod 40 of the movable lens unit 32 has moved to the telescopic end position T, the magnet 75 can attract the connection rod 40 with a force that is greater than or equal to an urging force in the forward direction that acts on the connection rod 40 when the helical compression spring 57 contracts.

Next, an action by the actuator 62 in the image pickup unit 30 configured as described above that causes the movable lens unit 32 to move forward or backward is described based on FIG. 8 and FIG. 15A to FIG. 18B. In the following description, a detailed description of driving control of the actuator 62 is simplified for convenience since the action is the same as the action of the actuator 62 in the first and second embodiments described above.

As shown in FIGS. 15A, 15B, a state in which the movable lens unit 32 is at the wide end position W based on the front end face of the connection rod 40 and an electric current is not being applied from the video processor 4 to the SMA wire 56 of the actuator 62 is a wide state of the image pickup unit 30 of the endoscope 2 of the present embodiment that is the initial state thereof In this case also, as shown in the curve graph in FIG. 8, an expansion/contraction state varies according to two curve relationships that represent deformation amounts by which the SMA wire 56 contracts with respect to a temperature increase produced by an applied electric current. These two curve relationships are represented by a curve with a so-called hysteresis curve shape at the time of electric current application and a curve at a time that an electric current is not applied.

When an operation is performed to switch the image pickup unit 30 from wide zooming to telescopic zooming, the actuator 62 is drivingly controlled so that the SMA wire 56 contracts and the connection rod 40 is urged rearward by the urging force of the helical compression spring 66 so that the movable lens unit 32 moves rearward while still contacting against the anchor 65.

At this time, the movable lens unit 32 moves rearward while the connection rod 40 is being guided in a straight line by the notch portion 36*a* of the rear group lens frame 36. In such case, as shown in FIGS. 16A, 16B, the rearward movement of the movable lens unit 32 is restricted and stopped by the rear end face of the connection rod 40 butting against the front end face of the restriction portion 36*t*. In this case, the movable lens unit 32 moves as far as the telescopic end position T that is based on the front end face of the connection rod 40.

This state is represented by the position denoted by reference characters a3 on the curve at the time of electric current application in FIG. 8. More specifically, by further contracting as far as the deformation amount Wa2 from the deformation amount Wa1 (contracting further by deformation amount Wa) due to application of an electric current of a predetermined ampere amount (number) that causes the SMA wire 56 to reach a temperature ta3, the SMA wire 56 is contracted to a predetermined length.

Further, in this state, the connection rod 40 attaches to the magnet 75 arranged at the restriction portion 36*t*, so that the movable lens unit 32 reliably moves to the telescopic end position T that is based on the front end face of the connection rod 40.

When the image pickup unit 30 is in the telescopic state, the shape memory alloy resistance control circuit portion 100 of the video processor 4 temporarily stops application of the current to the SMA wire 56 of the actuator 62. Thereupon, the SMA wire 56 expands by natural cooling to enter a slack state as shown in FIGS. 17A, 17B. The relationship between the temperature and deformation amount of the SMA wire 56 corresponds to the position denoted by reference characters b1 on the curve at the time of non-application of a current shown in FIG. 8.

At this time, the connection rod 40 is attracted to the magnet 75 arranged at the restriction portion 36*t* so that even if a forward urging force of the helical compression spring 57 acts indirectly through the anchor 65, the movable lens unit 32 does not move forward from the telescopic end position T that is based on the front end face of the connection rod 40.

That is, as described above, when the front end face of the connection rod 40 of the movable lens unit 32 has moved to the telescopic end position T, the magnetic force of the magnet 75 attracts the connection rod 40 with a force that is greater than or equal to the forward urging force that acts on the connection rod 40 when the helical compression spring 57 contracts, and further, a rearward urging force of the helical compression spring 66 acts on the connection rod 40 of the movable lens unit 32. Therefore, the movable lens unit 32 is stably stopped without moving forward from the telescopic end position T that is based on the front end face of the connection rod 40. Thus, the image pickup unit 30 of the endoscope 2 is switched from wide zooming to telescopic zooming.

Further, in the endoscope 2 of the present embodiment, when switching from a telescopic state to perform wide zooming to a subject, application of an electric current to the SMA wire 56 of the actuator 62 from the shape memory alloy resistance control circuit portion 100 of the video processor 4 is executed instantaneously. An electric current of a predetermined ampere amount (number) is instantaneously applied to the SMA wire 56 so that the temperature thereof exceeds by a large margin the temperature ta3 at the position denoted by reference characters a3 on the curve at the time of electric current application in FIG. 8. The image pickup unit 30 enters a state as shown in FIGS. 18A, 18B in which the SMA wire 56 contracts and the connection rod 40 and the anchor 65 are separated.

Thereafter, when the SMA wire 56 is at a temperature that exceeds by a large margin the temperature ta3, application of the electric current to the SMA wire 56 of the actuator 62 from the shape memory alloy resistance control circuit portion 100 of the video processor 4 is stopped. Thereupon, accompanying natural cooling and expansion of the SMA wire 56, the anchor 65 moves forward vigorously under the urging force of the helical compression spring 57 and collides with the connection rod 40 of the movable lens unit 32 so that the forward urging force of the helical compression spring 57 acts on the connection rod 40.

At this time, a repulsive stress (urging force) that is greater than the magnetic force of the magnet 75 to which the connection rod 40 is attracted and the rearward urging force of the helical compression spring 66 acts on the connection rod 40 of the movable lens unit 32 to move the connection rod 40 forward so that the connection rod 40 separates from the magnet 75.

Further, in the image pickup unit 30, by the connection rod 40 of the movable lens unit 32 being urged forward indirectly via the anchor 65 by a forward urging force of the helical compression spring 57 against the rearward urging force of the helical compression spring 66, the movable lens unit 32 moves to the wide end position W that is based on the front end face of the connection rod 40 in the state shown in FIGS. 15A, 15B. Thus, the image pickup unit 30 of the endoscope 2 is switched from telescopic to wide zooming.

According to the image pickup unit 30 of the endoscope system 1 of the present embodiment described above, similarly to the advantages of the first and second embodiments, forward and backward movement of the movable lens unit 32 that switches between wide zooming and telescopic zooming can be stably performed and the expansion/contraction response speed of the SMA wire 56 can be quickened. In this connection, the expansion/contraction response speed of the SMA wire 56 becomes slower, although only to a slight extant, at the time of telescopic or wide zooming.

However, because the image pickup unit 30 of the present embodiment is provided with the magnet 75 that attracts the movable lens unit 32, application of an electric current to the SMA wire 56 of the actuator 62 can be stopped at times other than the moments when the movable lens unit 32 moves backward or forward. That is, when the image pickup unit 30 is fixed in a telescopic or wide state an electric current is not passed to the SMA wire 56 of the actuator 62, and it is therefore possible to prevent damage to other members caused by heat generation of the SMA wire 56.

In particular, the temperature of the SMA wire 56 is high when the image pickup unit 30 is in a telescopic state. Consequently, in the telescopic state it is necessary to constantly pass an electric current to the SMA wire 56 to maintain a high temperature. There is thus a possibility that a fault will occur due to heat from the SMA wire 56 being conveyed to another member at that time. However, according to the image pickup unit 30 of the present embodiment, since an electric current is passed to the SMA wire 56 only for a short time when switching between a wide and a telescopic state, the effect of heat from the SMA wire 56 that is imparted to other members is reduced. It is thus possible to prevent damage to other members.

Fourth Embodiment

Next, the fourth embodiment of the present invention is described based on FIG. 19A to FIG. 24B.

FIG. 19A to FIG. 24B relate to the fourth embodiment of the present invention. FIGS. 19A, 19B are sectional views illustrating the configuration of an image pickup unit. FIGS. 20A, 20B are sectional views of the image pickup unit for describing an action whereby a movable lens frame moves to a telescopic end position. FIGS. 21A, 21B are sectional views of the image pickup unit that illustrate a state in which application of a current to an SMA wire is stopped in a state in which the movable lens frame has moved to the telescopic end position. FIGS. 22A, 22B are sectional views of the image pickup unit that illustrate a state in which the current is applied to the SMA wire again, in a state in which the movable lens frame has moved to the telescopic end position. FIGS. 23A, 23B are sectional views of the image pickup unit for describing an action in which the movable lens frame moves to an arbitrary optical property position. FIGS. 24A, 24B are sectional views of the image pickup unit that illustrate a state in which application of an electric current to the SMA wire is stopped in a state in which the movable lens frame has moved to an arbitrary optical property position.

In the following description, the same reference numerals are used for components that are the same as components of the image pickup unit 30 of the endoscope system 1 of the first to third embodiments described above, and a detailed description thereof is omitted. Further, instead of the magnet 75 of the image pickup unit 30 of the third embodiment, the image pickup unit of the present embodiment as described below is provided with an elastic ring-shaped frictional member constituting a frictional body, and has a configuration which stops the anchor 65 at an arbitrary position.

As shown in FIGS. 19A, 19B, the image pickup unit 30 of the present embodiment is provided with a ring-shaped frictional member 80 formed of an elastic body such as rubber on the outer circumference of the rear group lens frame 36. The frictional member 80 is arranged so that a front end face thereof is positioned in the same plane as the front end face of the restriction portion 36t of the rear group lens frame 36 that defines the telescopic end position T that is based on the front end face of the connection rod 40. The image pickup unit 30 is configured such that the anchor 65 connected to the SMA wire 56 can be subjected to braking to stop the anchor 65 at an arbitrary position with a predetermined frictional force when the anchor 65 touches the frictional member 80.

The frictional member 80 is not limited to a ring shape, and can be any shape as long as the frictional member 80 generates a predetermined frictional force upon touching the anchor 65. The remaining configuration is substantially the same as in the image pickup unit 30 of the second and third embodiments.

The image pickup unit 30 is also provided with a rail member 81 that is made of metal. The rail member 81 extends from the front lower portion of the actuator retention portion 52. The anchor 65 contacts with the rail member 81 and slides thereon. That is, the anchor 65 that moves forward and rearward on the rail member 81 enters a state in which the anchor 65 is sandwiched between the rail member 81 and the frictional member 80 within the range in which the frictional member 80 is provided, and the configuration is such that the frictional member 80 touches the anchor 65 with a predetermined frictional force.

Next, an action by the actuator 62 in the image pickup unit 30 configured as described above that causes the movable lens unit 32 to move forward and backward is described based on FIG. 19A to FIG. 24B. In the following description, a detailed description of driving control of the actuator 62 is simplified for convenience since the action is the same as the action of the actuator 62 in the third embodiment described above.

As shown in FIGS. 19A, 19B, when an operation is performed to switch the image pickup unit 30 of the endoscope 2 of the present embodiment from wide to telescopic zooming, the actuator 62 is drivingly controlled so that the SMA wire 56 contracts and the connection rod 40 is urged rearward by the urging force of the helical compression spring 66 such that movable lens unit 32 moves rearward while remaining in contact against the anchor 65.

At this time, the anchor 65 that is pulled by the SMA wire 56 moves rearward while sliding on the rail member 81, and touches against the frictional member 80 such that a predetermined frictional force is imparted to an upper part on the outer circumference of the anchor 65. In this state, the movable lens unit 32 moves rearward while the connection rod 40 is being guided in a straight line by the notch portion 36a of the rear group lens frame 36. In such case, as shown in FIGS. 20A, 20B, the rearward movement of the movable lens unit 32 is restricted and stopped by the rear end face of the connection rod 40 butting against the front end face of the restriction portion 36t. In this case, the movable lens unit 32 moves as far as the telescopic end position T that is based on the front end face of the connection rod 40.

Further, similarly to the third embodiment, when the image pickup unit 30 is in the telescopic state, the shape memory alloy resistance control circuit portion 100 of the video processor 4 temporarily stops application of the electric current to the SMA wire 56 of the actuator 62. Thereupon, the SMA wire 56 expands by natural cooling to enter a slack state as shown in FIGS. 21A, 21B.

At this time, even in a state in which a forward urging force is being applied to the anchor 65 by the helical compression spring 57, the anchor 65 is sandwiched between the rail member 81 and the frictional member 80 and enters a stopped state as the result of the predetermined frictional force produced by contact with the frictional member 80. That is, in a state in which the movable lens unit 32 has moved to the telescopic end position T that is based on the front end face of the connection rod 40, the predetermined frictional force that acts from the frictional member 80, in addition to the rearward urging force produced by the helical compression spring 66, is set to be greater than the forward urging force of the helical compression spring 57, and thus the anchor 65 stops.

More specifically, the movable lens unit 32 is in a state in which the connection rod 40 is contacting against the restriction portion 36t, and a forward urging force of the helical compression spring 57 is not acting thereon indirectly from the anchor 65 and, further, the movable lens unit 32 is being urged to the rearward side by the urging force of the helical compression spring 66. Accordingly, the movable lens unit 32 is in a stably stopped state in which the movable lens unit 32 does not move forward from the telescopic end position T that is based on the front end face of the connection rod 40. Thus, the image pickup unit 30 of the endoscope 2 is switched from wide to telescopic zooming.

Moreover, similarly to the third embodiment, in the endoscope 2 of the present embodiment application of an electric current to the SMA wire 56 of the actuator 62 from the shape memory alloy resistance control circuit portion 100 is executed instantaneously at the time of switching to wide zooming to a subject from a telescopic state. As shown in FIGS. 22A, 22B, the image pickup unit 30 is in a state in which the SMA wire 56 is contracted and the connection rod 40 and the anchor 65 are separated.

Thereafter, when the SMA wire 56 is at a temperature that exceeds by a large margin the temperature ta3, application of the electric current to the SMA wire 56 of the actuator 62 from the shape memory alloy resistance control circuit portion 100 of the video processor 4 is stopped. Thereupon, accompanying natural cooling and expansion of the SMA wire 56, the anchor 65 moves forward vigorously under the urging force of the helical compression spring 57 and collides with the connection rod 40 of the movable lens unit 32 so that the forward urging force of the helical compression spring 57 acts on the connection rod 40.

At this time, although the anchor 65 receives a predetermined frictional force through contact with the frictional member 80, a repulsive stress (urging force) of the helical compression spring 57 is greater than the predetermined frictional force and, furthermore, a stress that is greater than the rearward urging force of the helical compression spring 66 acts to move the anchor 65 forward so that the anchor 65 passes by the frictional member 80. Further, in the image pickup unit 30, by the connection rod 40 of the movable lens unit 32 being urged forward indirectly via the anchor 65 by a forward urging force of the helical compression spring 57 against the rearward urging force of the helical compression spring 66, the movable lens unit 32 moves to the wide end position W based on the front end face of the connection rod 40 in the state shown in FIGS. 19A, 19B. Thus, the image pickup unit 30 of the endoscope 2 is switched from telescopic to wide zooming.

As shown in FIGS. 23A, 23B, the image pickup unit 30 of the present embodiment can stop the movable lens unit 32 at an arbitrary zooming position Z between the telescopic end position T and the wide end position W based on the front end face of the connection rod 40 of the movable lens unit 32.

More specifically, in the image pickup unit 30, an electric current of a predetermined ampere amount (number) is applied to the SMA wire 56 of the actuator 62 by the shape memory alloy resistance control circuit portion 100 of the video processor 4 to heat the SMA wire 56 to a predetermined temperature, and the expansion/contraction state of the SMA wire 56 is controlled as far as an arbitrary zooming position Z based on the front end face of the connection rod 40 of the movable lens unit 32. In this state, as shown in FIGS. 23A, 23B, the anchor 65 stops at a predetermined position in which the anchor 65 is sandwiched by the rail member 81 and the frictional member 80.

Thereafter, when the image pickup unit 30 is in a telescopic state, the shape memory alloy resistance control circuit portion 100 of the video processor 4 temporarily stops application of the electric current to the SMA wire 56 of the actuator 62. Thereupon, the SMA wire 56 expands due to natural cooling and enters a slack state as shown in FIGS. 24A, 24B.

At this time also, in a state in which a forward urging force is being applied to the anchor 65 by the helical compression spring 57, the anchor 65 is sandwiched between the rail member 81 and the frictional member 80 and enters a stopped state as the result of the predetermined frictional force produced by contact with the frictional member 80. That is, as described above, in a state in which the movable lens unit 32 has moved to an arbitrary position Z that is based on the front end face of the connection rod 40, the predetermined frictional force that acts from the frictional member 80, in addition to the rearward urging force produced by the helical compression spring 66, is set to be greater than the forward urging force of the helical compression spring 57, and thus the anchor 65 stops.

Thus, according to the image pickup unit 30 of the present embodiment, the movable lens unit 32 can be stopped at an arbitrary position. It is therefore possible to vary an arbitrary optical property, in this case the optical magnitude.

In the case of moving the movable lens unit 32 in the telescopic direction (rearward) from the arbitrary position of the movable lens unit 32, an electric current is applied to the SMA wire 56 to cause the SMA wire 56 to contract. In contrast, when moving the movable lens unit 32 in the wide direction (forward) from the arbitrary position of the movable lens unit 32, as shown in FIGS. 22A, 22B, the SMA wire 56 is caused to contract to enter a state in which the connection rod 40 and the anchor 65 of the image pickup unit 30 are separated, and thereafter, as described above, by stopping application of the electric current to the SMA wire 56 the anchor 65 is caused to move forward vigorously due to the urging force of the helical compression spring 57.

Thereupon, the anchor 65 collides with the connection rod 40 of the movable lens unit 32 so that the forward urging force of the helical compression spring 57 acts on the connection rod 40 to move the connection rod 40 so that the movable lens unit 32 moves in the wide direction.

According to the image pickup unit 30 of the present embodiment configured as described above, in addition to the advantages of the third embodiment, it is possible to stop the movable lens unit 32 at an arbitrary position between the maximum wide and maximum telescopic zooming positions and thus arbitrarily vary the optical magnitude.

In this connection, although varying the optical magnitude between wide and telescopic zooming is described as an example of varying an optical property in each of the above embodiments, naturally the present invention can also be applied to controlling forward and backward movement of the movable lens unit to perform focal adjustment of the image pickup unit 30.

According to the invention described above, an actuator apparatus and an image pickup unit can be realized that can improve the responsiveness when varying an optical property by moving a movable lens frame forward or backward for a zooming function or the like, and can also stably and reliably move a movable lens forward or backward in conformity with an optical property that is set in the image pickup unit.

The invention described in the foregoing embodiments is not limited to those embodiments and modification examples, and various changes and modifications and the like are possible at the implementation stage without deviating from the spirit and scope of the present invention. Further, the embodiments include inventions of various stages, and various inventions can be extracted by appropriately combining a plurality of the disclosed configuration requirements.

For example, if a problem described herein as a problem to be overcome by the invention can be solved and if the effects described herein are still obtained after omitting some of the configuration requirements shown in the embodiments, then the configuration obtained by omitting the configuration requirements can be extracted as an embodiment of the invention.

What is claimed is:

1. An image pickup unit, comprising:
    a movable lens unit that has an optical lens and that moves the optical lens forward and backward in an optical axis direction;
    a first elastic member that urges the movable lens unit forward;
    a second elastic member that urges the movable lens unit backward, and that is provided on an axis that is parallel to and different from an axis of the first elastic member and that has a smaller urging force than the first elastic member; and
    a shape memory alloy wire that is provided directly or indirectly to the movable lens unit and that pulls the movable lens unit rearward at a time of contraction upon being subjected to expansion/contraction control in which an electric current is applied thereto from a power supply portion of an external control circuit portion to change a temperature thereof to a predetermined temperature.

2. The image pickup unit according to claim 1, wherein the shape memory alloy wire is provided so as to enter a non-tension state at a time of an ordinary temperature.

3. The image pickup unit according to claim 2, wherein the first elastic member and the second elastic member are arranged so as to urge the movable lens unit along an axis parallel to the optical axis direction.

4. The image pickup unit according to claim 2, wherein the shape memory alloy wire is connected to an indirect action member so as to act indirectly with the movable lens unit.

5. The image pickup unit according to claim 1, wherein the first elastic member and the second elastic member are arranged so as to urge the movable lens unit along an axis parallel to the optical axis direction.

6. The image pickup unit according to claim 5, wherein the shape memory alloy wire is connected to an indirect action member so as to act indirectly with the movable lens unit.

7. The image pickup unit according to claim 1, wherein the shape memory alloy wire is connected to an indirect action member so as to act indirectly with the movable lens unit.

8. The image pickup unit according to claim 7, further comprising:
    a magnet that attracts the movable lens unit so as to stop the movable lens unit at a predetermined movement end position against an urging force of the first elastic member or the second elastic member, irrespective of an expansion or contraction state of the shape memory alloy wire.

9. The image pickup unit according to claim 7, further comprising:
    a frictional member that stops the indirect action member that moves forward or rearward upon an expansion/contraction state of the shape memory alloy wire being controlled by the control circuit portion at an arbitrary position by means of a frictional force, to thereby stop the movable lens unit at an arbitrary forward or rearward position.

* * * * *